(12) United States Patent
Tanaka et al.

(10) Patent No.: US 10,932,753 B2
(45) Date of Patent: Mar. 2, 2021

(54) ULTRASOUND DIAGNOSIS APPARATUS AND METHOD FOR CORRECTING MIS-REGISTRATION OF IMAGE DATA WITH POSITION SENSORS

(71) Applicant: Toshiba Medical Systems Corporation, Otawara (JP)

(72) Inventors: Go Tanaka, Otawara (JP); Kazuya Akaki, Utsunomiya (JP); Osamu Nakajima, Otawara (JP); Masaru Ogasawara, Nasushiobara (JP); Shogo Fukuda, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1288 days.

(21) Appl. No.: 14/582,253

(22) Filed: Dec. 24, 2014

(65) Prior Publication Data

US 2015/0112196 A1  Apr. 23, 2015

Related U.S. Application Data

(63) Continuation of application No. PCT/JP2013/067563, filed on Jun. 26, 2013.

(30) Foreign Application Priority Data

Jun. 27, 2012 (JP) .............................. JP2012-143824
Jun. 26, 2013 (JP) .............................. JP2013-134193

(51) Int. Cl.
*A61B 8/00* (2006.01)
*A61B 5/06* (2006.01)
*A61B 8/08* (2006.01)

(52) U.S. Cl.
CPC ............ *A61B 8/4245* (2013.01); *A61B 5/065* (2013.01); *A61B 8/4254* (2013.01); *A61B 8/463* (2013.01);

(Continued)

(58) Field of Classification Search
CPC ..... A61B 8/4245; A61B 8/5261; A61B 8/466; A61B 8/4254; A61B 8/463; A61B 5/065; A61B 8/483

See application file for complete search history.

(56) References Cited

U.S. PATENT DOCUMENTS 8,348,846 B2 * 1/2013 Gunther ................... A61B 8/08
600/424
2002/0133098 A1 * 9/2002 Shechtman ............ A61B 5/064
600/594

(Continued)

FOREIGN PATENT DOCUMENTS

JP  10-151131 A   6/1998
JP  10-151131 A5  6/1998

(Continued)

OTHER PUBLICATIONS

Chen, Elvis, et al. Ultrasound guided spine needle insertion. Diss. University of British Columbia, 2010.*

(Continued)

*Primary Examiner* — Serkan Akar
(74) *Attorney, Agent, or Firm* — Oblon, McClelland, Maier & Neustadt, L.L.P.

(57) ABSTRACT

According to an embodiment, a transmitter transmits a reference signal. A position sensor obtains position information in a three-dimensional space by receiving the reference signal. A controlling unit associates three-dimensional image data generated by a medical image diagnosis apparatus with the three-dimensional space, on the basis of a registration between an arbitrary cross-sectional plane in the three-dimensional image data and a cross-sectional plane (Continued)

scanned by an ultrasound probe. A detecting unit detects if the position of the transmitter has changed within the associated three-dimensional space, on the basis of the position information obtained by the position sensor. A correcting unit corrects a misregistration between a cross-sectional plane in the three-dimensional image data and a cross-sectional plane scanned by the ultrasound probe, on the basis of a change amount of the position of the transmitter.

10 Claims, 11 Drawing Sheets

(52) U.S. Cl.
CPC ............ *A61B 8/466* (2013.01); *A61B 8/5261* (2013.01); *A61B 8/483* (2013.01)

(56) References Cited

U.S. PATENT DOCUMENTS

| | | | |
|---|---|---|---|
| 2007/0010743 A1* | 1/2007 | Arai | ........................... G06T 7/33 600/443 |
| 2012/0179040 A1 | 7/2012 | Arai et al. | |
| 2012/0184851 A1 | 7/2012 | Arai et al. | |
| 2012/0184852 A1 | 7/2012 | Arai et al. | |
| 2013/0150709 A1* | 6/2013 | Baumgartner | ..... A61B 17/8866 600/424 |
| 2014/0343428 A1 | 11/2014 | Tanaka et al. | |

FOREIGN PATENT DOCUMENTS

| | | |
|---|---|---|
| WO | WO 2004/098414 A1 | 11/2004 |
| WO | WO 2006/068103 A1 | 6/2006 |
| WO | WO 2012/082861 A2 | 6/2012 |
| WO | WO2013101562 * | 12/2012 |

OTHER PUBLICATIONS

Much (Error Classification and Propagation for Electromagnetic Tracking) (Year: 2008).*
Combined Office Action and Search Report dated Dec. 3, 2015 in Chinese Patent Application No. 201380032661.6 with English translation of category of cited documents.
International Search Report dated Jul. 30, 2013 for PCT/JP2013/067563 Filed on Jun. 26, 2013 (English Language).
International Written Opinion dated Jul. 30, 2013 for PCT/JP2013/067563 Filed on Jun. 26, 2013.
U.S. Appl. No. 14/446,677, filed Jul. 30, 2014, 2014-0343428, Tanaka, et al.

* cited by examiner

FIG.3
(A)
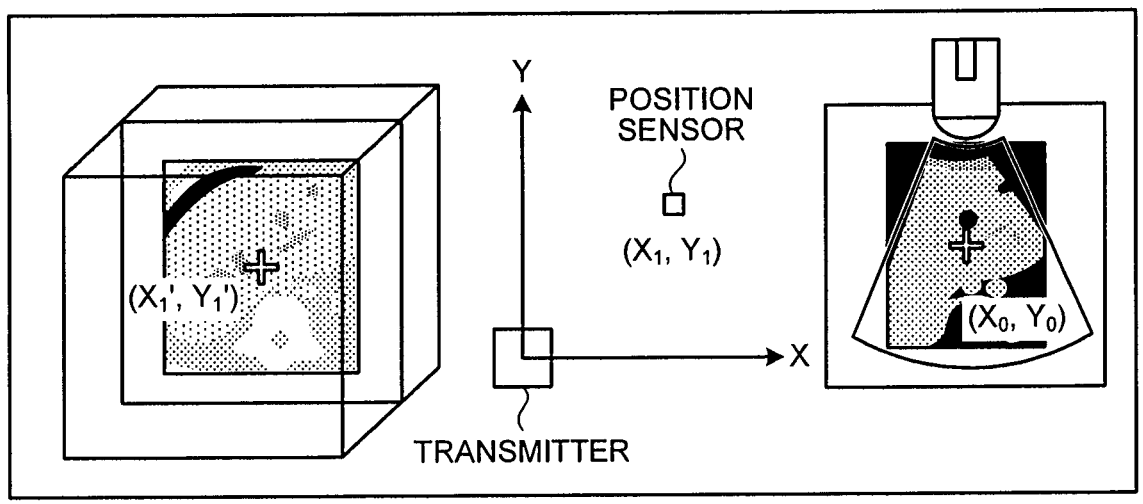
(B)
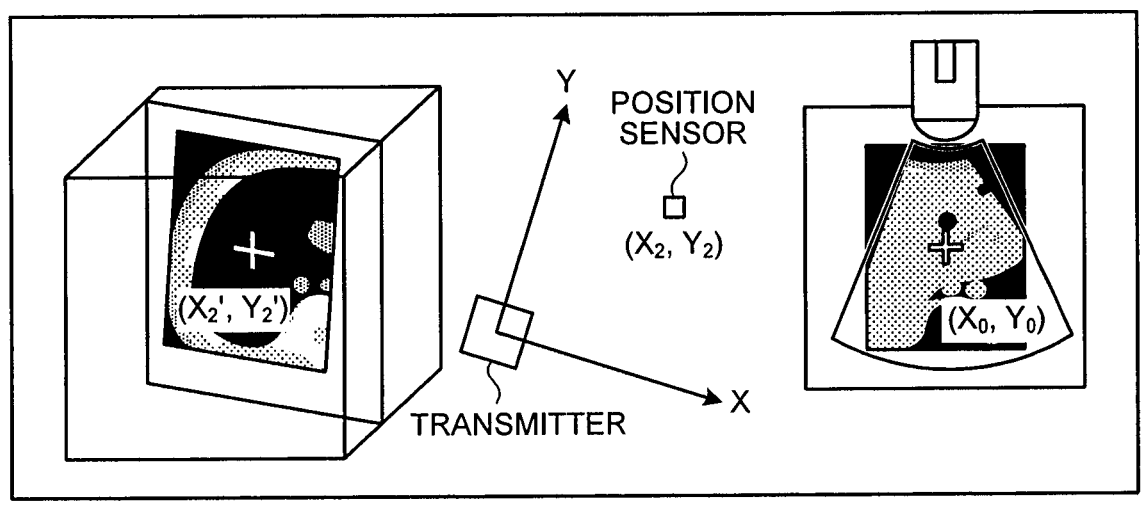

FIG.5
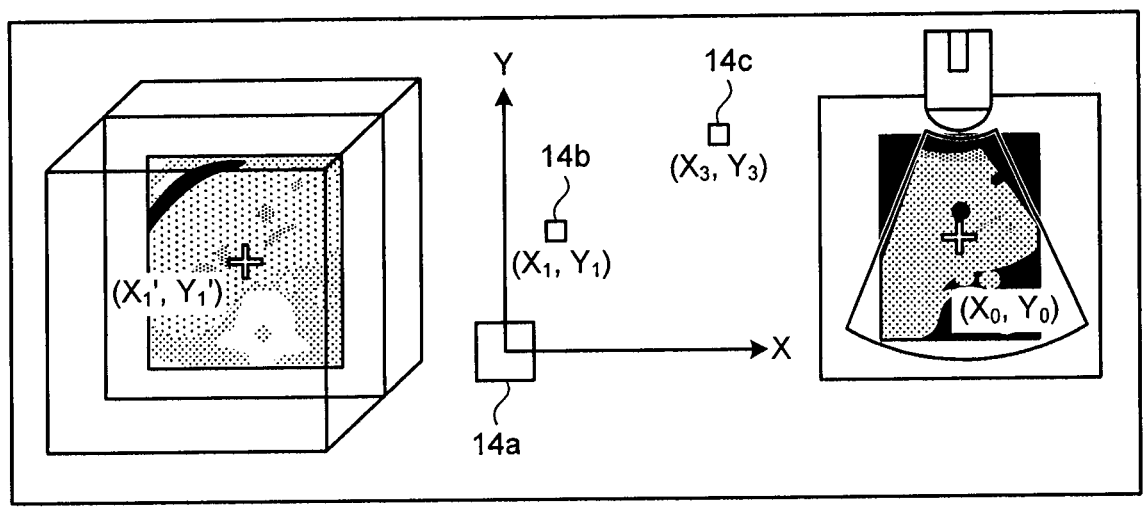
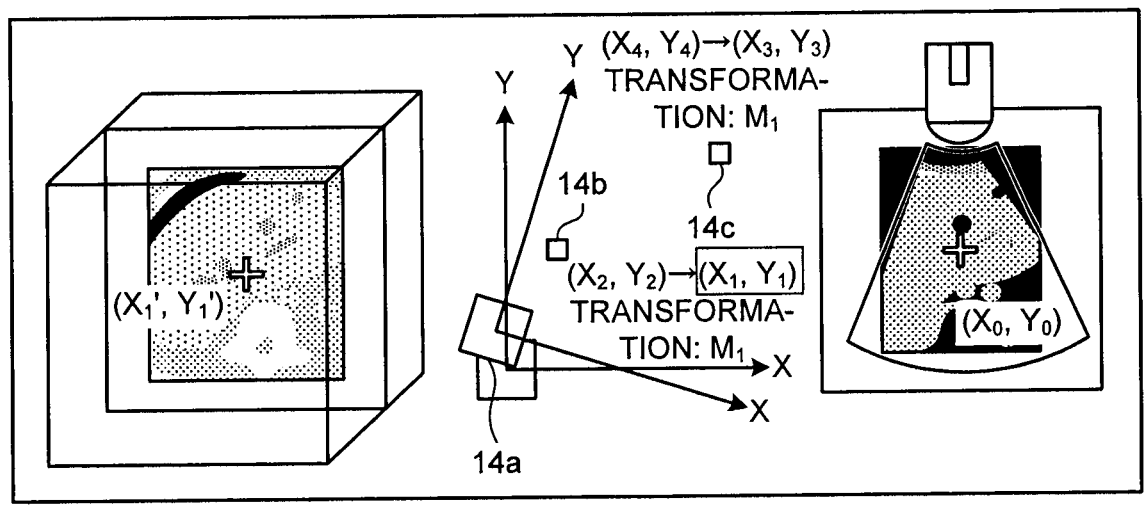

FIG.6
(A)
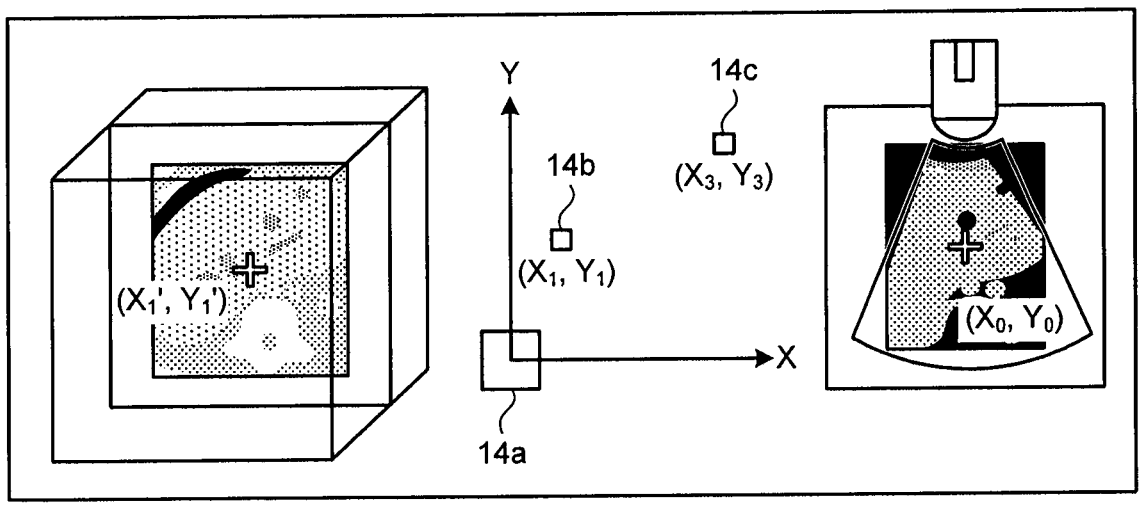
(B)
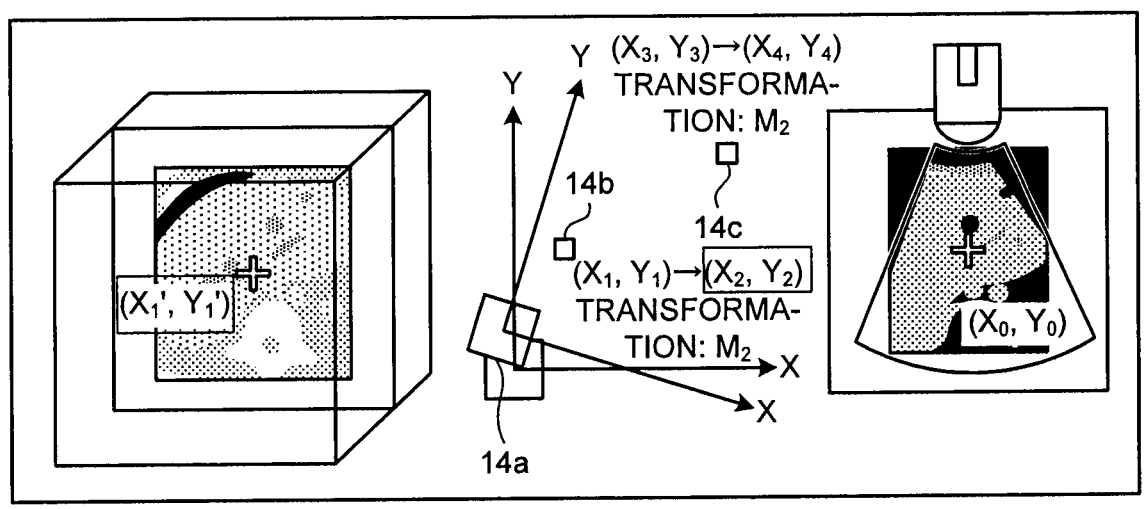

FIG.10
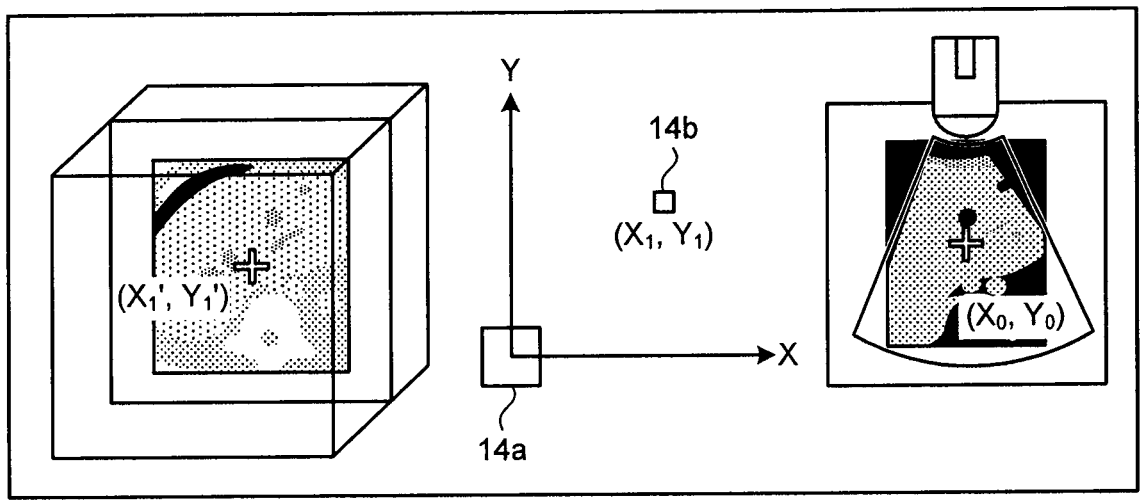
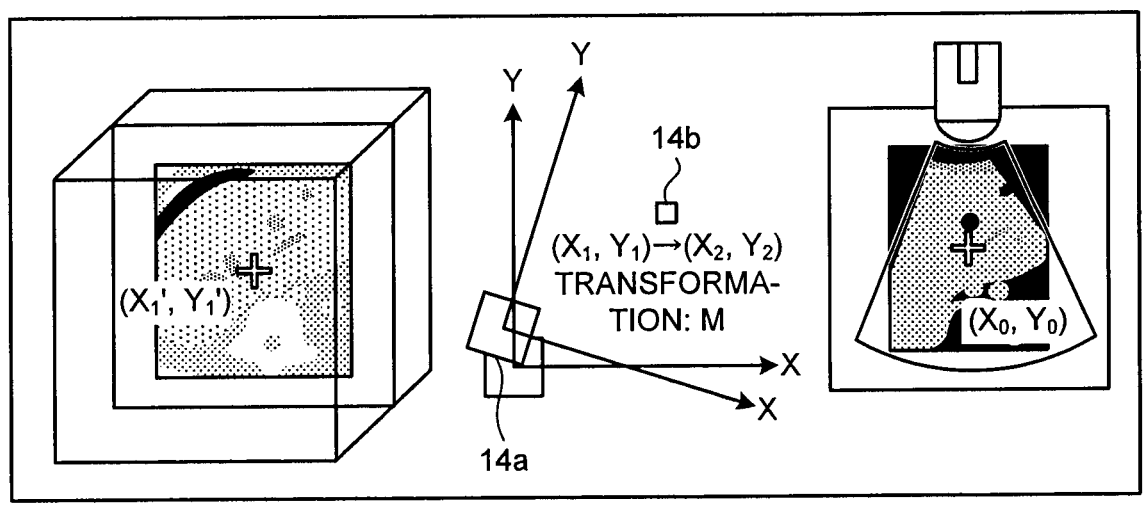

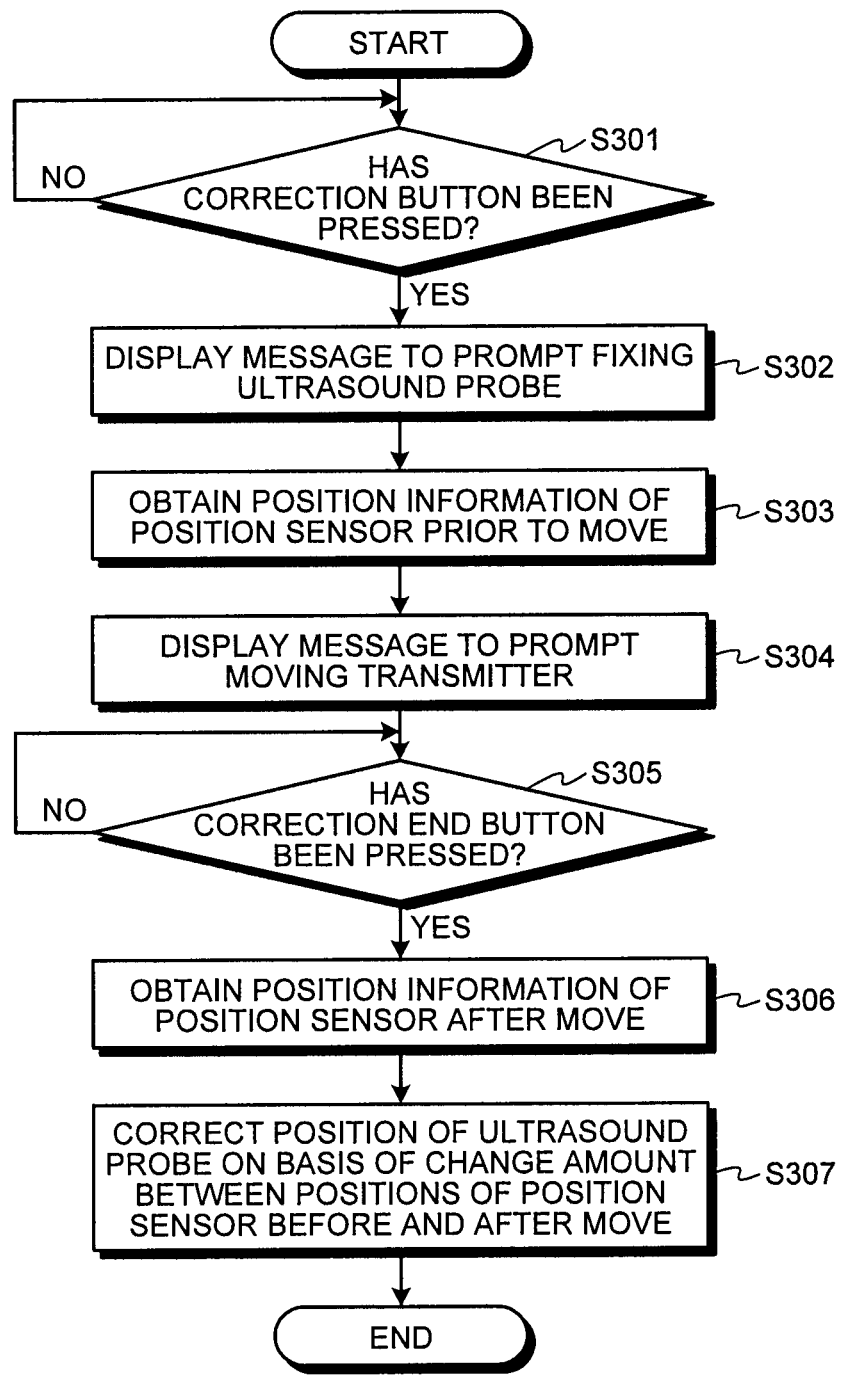

ULTRASOUND DIAGNOSIS APPARATUS AND METHOD FOR CORRECTING MIS-REGISTRATION OF IMAGE DATA WITH POSITION SENSORS

CROSS-REFERENCE TO RELATED APPLICATIONS

This application is a continuation of PCT international application Ser. No. PCT/JP2013/067563 filed on Jun. 26, 2013 which designates the United States, incorporated herein by reference, and which claims the benefit of priority from Japanese Patent Application No. 2012-143824, filed on Jun. 27, 2012 and Japanese Patent Application No. 2013-134193, filed on Jun. 26, 2013, the entire contents of which are incorporated herein by reference.

FIELD

Embodiments described herein relate generally to an ultrasound diagnosis apparatus and a method for correcting image data.

BACKGROUND

Conventionally, ultrasound diagnosis apparatuses are used as non-invasive diagnosis apparatuses for making observations on a regular basis of subjects suffering from a disease having a high risk for cancer. For example, ultrasound image diagnosis apparatuses are used for making observations on a regular basis of subjects suffering from a disease having a high risk for liver cancer, such as hepatitis or hepatic cirrhosis.

In recent years, a medical examination employing an X-ray Computed Tomography (CT) apparatus or a Magnetic Resonance Imaging (MRI) apparatus is performed in parallel with making observations using an ultrasound diagnosis apparatus as described above. For example, as for medical examinations using an X-ray CT apparatus or an MRI apparatus, a lesion that exhibits a possibility of cancer may be found during a medical examination using a contrast agent. In that situation, a definite diagnosis is made, in more and more occasions, after cytodiagnosis is performed by puncturing the lesion while using an ultrasound image.

In this regard, an ultrasound diagnosis apparatus is known, for example, that uses a technique by which a cross-sectional plane scanned by an ultrasound probe is positionally aligned with a CT image or an MRI image from which the lesion has been detected while employing a magnetic position sensor so that the ultrasound probe is navigated to the position of the lesion while using the CT image or the MRI image as a reference image. According to this conventional technique, however, it is necessary to perform the registration every time a transmitter moves, and the efficiency of the diagnosis process is lowered in some situations.

BRIEF DESCRIPTION OF THE DRAWINGS

FIG. 3 is a drawing for explaining a problem with a conventional technique;

FIG. 5 is a drawing for explaining an example of a first correcting process according to the first embodiment;

FIG. 6 is a drawing for explaining an example of a second correcting process according to the first embodiment;

FIG. 10 is a drawing for explaining an example of a correcting process according to a third embodiment; and FIG. 11 is a flowchart of a procedure in a process performed by an ultrasound diagnosis apparatus according to the third embodiment.

DETAILED DESCRIPTION

According to embodiment, an ultrasound diagnosis apparatus comprising, a transmitter, a position sensor, an associating unit, a detecting unit and a correcting unit. The transmitter transmits a reference signal. The position sensor that obtains position information in a three-dimensional space by receiving the reference signal. The an associating unit that associates three-dimensional image data generated by a medical image diagnosis apparatus with the three-dimensional space, on a basis of a registration between an arbitrary cross-sectional plane in the three-dimensional image data and a cross-sectional plane scanned by an ultrasound probe. The detecting unit that detects if a position of the transmitter has changed within the associated three-dimensional space, on a basis of the position information obtained by the position sensor. The correcting unit that, when the change in the position of the transmitter has been detected, corrects a misregistration between a cross-sectional plane in the three-dimensional image data and a cross-sectional plane scanned by the ultrasound probe, on a basis of a change amount of the position of the transmitter.

Figure 1:
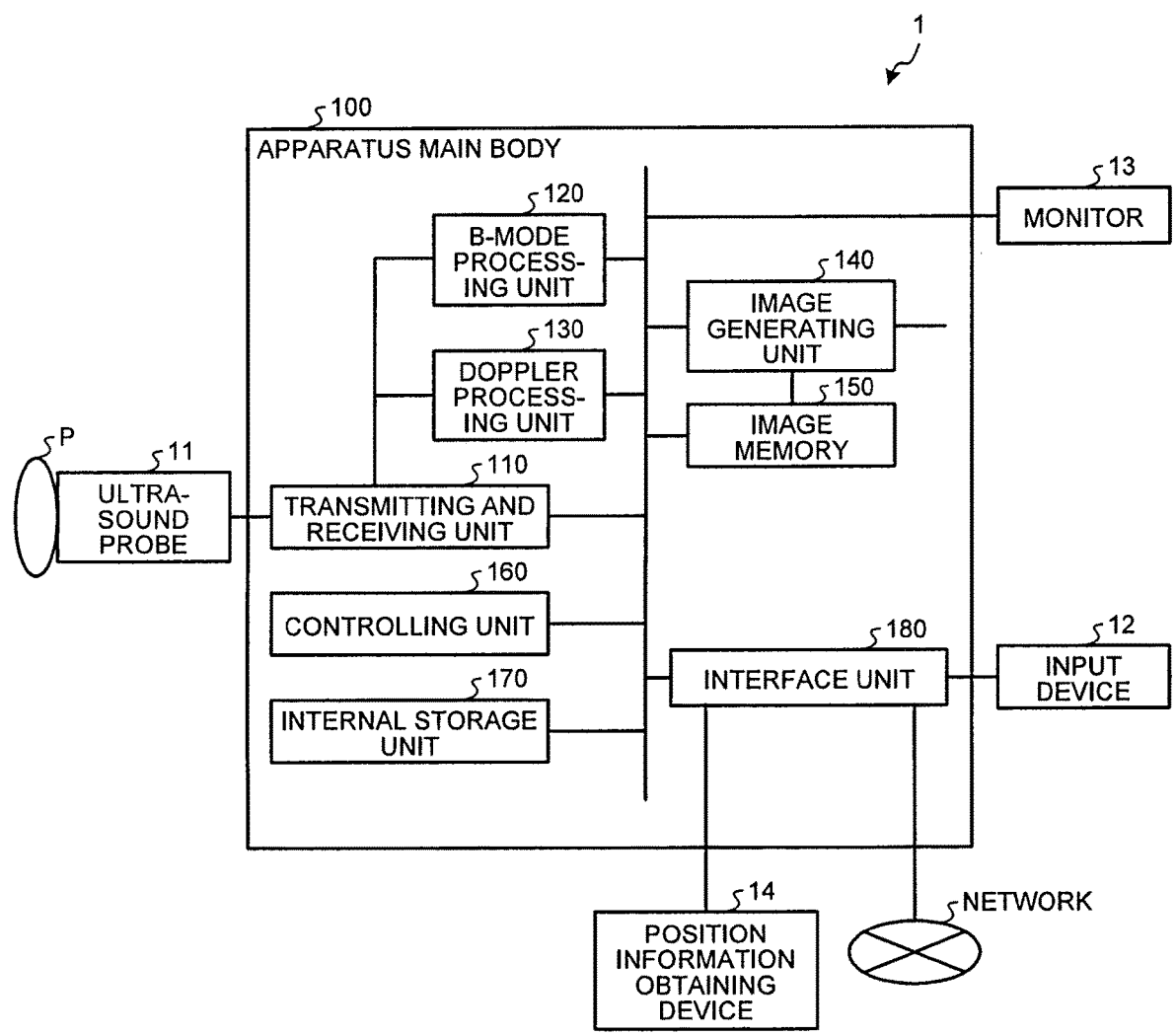
FIG. 1 is a drawing for explaining an overall configuration of an ultrasound diagnosis apparatus according to a first embodiment.

First, an overall configuration of an ultrasound diagnosis apparatus according to a first embodiment will be explained, with reference to FIG. 1. FIG. 1 is a drawing for explaining an overall configuration of an ultrasound diagnosis apparatus 1 according to the first embodiment. As shown in FIG. 1, the ultrasound diagnosis apparatus 1 according to the first embodiment includes an ultrasound probe 11, an input device 12, a monitor 13, a position information obtaining device 14, and an apparatus main body 100 and is connected to a network.

The ultrasound probe 11 includes a plurality of piezoelectric transducer elements, which generate an ultrasound wave based on a drive signal supplied from a transmitting and receiving unit 110 included in the apparatus main body 100 (explained later) and which further receive a reflected wave from an examined subject P and convert the received reflected wave into an electric signal. Further, the ultrasound probe 11 includes matching layers included in the piezoelectric transducer elements, as well as a backing member that prevents ultrasound waves from propagating rearward from the piezoelectric transducer elements. For example, the ultrasound probe 11 is an ultrasound probe of a sector-type, a linear-type, or a convex-type.

When an ultrasound wave is transmitted from the ultrasound probe 11 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 11. The amplitude of the received reflected-wave signal is dependent on the difference between the acoustic impedances on the surface of discontinuity on which the ultrasound wave is reflected. When the transmitted ultrasound pulse is reflected on the surface of a flowing bloodstream or a cardiac wall, the reflected-wave signal is, due to the Doppler effect, subject to a frequency shift, depending on a velocity component of the moving members with respect to the ultrasound wave transmission direction.

The first embodiment is applicable to a situation where the subject P is two-dimensionally scanned by using the ultrasound probe 11 that is a one-dimensional ultrasound probe in which the plurality of piezoelectric transducer elements are arranged in a row or to a situation where the subject P is three-dimensionally scanned by using the ultrasound probe 11 that is configured to mechanically swing the plurality of piezoelectric transducer elements provided in a one-dimensional ultrasound probe or by using the ultrasound probe 11 that is configured with a two-dimensional ultrasound probe in which the plurality of piezoelectric transducer elements are two-dimensionally arranged in a grid formation.

The input device 12 includes a trackball, a switch, a button, a touch command screen, and the like. The input device 12 is configured to receive various types of setting requests from an operator of the ultrasound diagnosis apparatus 1 and to transfer the received various types of setting requests to the apparatus main body 100. For example, the input device 12 receives various types of operations related to a registration between an ultrasound image and an X-ray CT image or the like.

The monitor 13 is configured to display a Graphical User Interface (GUI) used by the operator of the ultrasound diagnosis apparatus 1 to input the various types of setting requests through the input device 12 and to display an ultrasound image generated by the apparatus main body 100 side by side with an X-ray CT image or the like.

The position information obtaining device 14 is configured to obtain position information of the ultrasound probe 11. More specifically, the position information obtaining device 14 obtains the position information indicating where the ultrasound probe 11 is positioned. Examples of the position information obtaining device 14 include a magnetic sensor, an infrared sensor, an optical sensor, and a camera.

The apparatus main body 100 is an apparatus configured to generate the ultrasound image based on the reflected wave received by the ultrasound probe 11. As shown in FIG. 1, the apparatus main body 100 includes the transmitting and receiving unit 110, a B-mode processing unit 120, a Doppler processing unit 130, an image generating unit 140, an image memory 150, a controlling unit 160, an internal storage unit 170, and an interface unit 180.

The transmitting and receiving unit 110 includes a trigger generating circuit, a delaying circuit, a pulser circuit, and the like and is configured to supply the drive signal to the ultrasound probe 11. The pulser circuit repeatedly generates a rate pulse for forming a transmission ultrasound wave at a predetermined rate frequency. Further, the delaying circuit applies a delay period that is required to converge the ultrasound wave generated by the ultrasound probe 11 into the form of a beam and to determine transmission directionality and that corresponds to each of the piezoelectric transducer elements, to each of the rate pulses generated by the pulser circuit. Further, the trigger generating circuit applies a drive signal (a drive pulse) to the ultrasound probe 11 with timing based on the rate pulses. In other words, the delaying circuit arbitrarily adjusts the directions of the transmissions from the piezoelectric transducer element surfaces, by varying the delay periods applied to the rate pulses.

Further, the transmitting and receiving unit 110 includes an amplifier circuit, an Analog/Digital (A/D) converter, an adder, and the like and is configured to generate reflected-wave data by performing various types of processes on the reflected-wave signal received by the ultrasound probe 11. The amplifier circuit amplifies the reflected-wave signal for each of channels and performs a gain correcting process thereon. The A/D converter applies an A/D conversion to the gain-corrected reflected-wave signal and applies a delay period required to determine reception directionality thereto. The adder performs an adding process on the reflected-wave signals processed by the A/D converter so as to generate the reflected-wave data. As a result of the adding process performed by the adder, reflected components from the direction corresponding to the reception directionality of the reflected-wave signals are emphasized.

As explained above, the transmitting and receiving unit 110 controls the transmission directionality and the reception directionality in the transmissions and receptions of the ultrasound waves. The transmitting and receiving unit 110 has a function to be able to, under control of the controlling unit 160 (explained later), instantly change the delay information, the transmission frequency, the transmission drive voltage, the number of aperture elements, and the like. In particular, the configuration to change the transmission drive voltage is realized by using a linear-amplifier-type oscillation circuit of which the value can be instantly switched or by using a mechanism configured to electrically switch between a plurality of power source units. Further, the transmitting and receiving unit 110 is also capable of transmitting and receiving a waveform that varies for each of the frames or for each of different rates.

The B-mode processing unit 120 is configured to receive, from the transmitting and receiving unit 110, the reflected-wave data, which is represented by the processed reflected-wave signals on which the gain correcting process, the A/D conversion, and the adding process were performed, and to further generate data (B-mode data) in which the strength of each signal is expressed by a degree of brightness, by performing a logarithmic amplification, an envelope detection process, and the like on the received reflected-wave data.

The Doppler processing unit 130 is configured to extract bloodstreams, tissues, and contrast-agent echo components under the influence of the Doppler effect by performing a frequency analysis so as to obtain velocity information from the reflected-wave data received from the transmitting and receiving unit 110, and to further generate data (Doppler data) obtained by extracting moving member information such as an average velocity, a dispersion, a power, and the like for a plurality of points.

The image generating unit 140 is configured to generate an ultrasound image from the B-mode data generated by the B-mode processing unit 120 or from the Doppler data generated by the Doppler processing unit 130. More specifically, the image generating unit 140 generates a display-purpose ultrasound image (a B-mode image or a Doppler image) from the B-mode data or the Doppler data, by converting (by performing a scan convert process) a scanning line signal sequence from an ultrasound scan into a scanning line signal sequence in a video format used by, for example, television. Further, under control of the controlling unit 160 (explained later), the image generating unit 140 is configured to generate a two-dimensional image (e.g., a Multi-Planar Reconstruction [MPR] image) from volume data in another imaging modality stored in the internal storage unit 170.

The image memory 150 is configured to store therein image data generated by the image generating unit 140 such as a contrast enhanced image and/or a tissue image. Further, the image memory 150 is configured to store therein data of the two-dimensional image (e.g., an MPR image) in another imaging modality generated by the image generating unit 140. Further, the image memory 150 is configured to store therein results of processes performed by the image generating unit 140 (explained later). Furthermore, the image memory 150 is configured to store therein, as necessary, output signals (radio frequency [RF]) immediately output from the transmitting and receiving unit 110, brightness-level signals of images, various types of raw data, image data obtained via a network, and the like. The data format of the image data stored in the image memory 150 may be a data format resulting from a video format conversion intended for the display on the monitor 13 realized under the control of the controlling unit 160 (explained later) or may be a data format prior to a coordinate transformation that is represented by raw data generated by the B-mode processing unit 120 and the Doppler processing unit 130.

The controlling unit 160 is configured to control overall processes performed by the ultrasound diagnosis apparatus 1. More specifically, based on the various types of setting requests input by the operator via the input device 12 and various types of control computer programs (hereinafter, "control programs") and various types of setting information read from the internal storage unit 170, the controlling unit 160 controls processes performed by the transmitting and receiving unit 110, the B-mode processing unit 120, the Doppler processing unit 130, and the image generating unit 140, and also exercises control so that the monitor 13 displays the ultrasound image and the like stored in the image memory 150. Further, the controlling unit 160 is configured to transmit and receive, via a network, three-dimensional image data (volume data) in another imaging modality (using, for example, an X-ray CT apparatus or an MRI apparatus), according to the specifications of the Digital Imaging and Communications in Medicine (DICOM), for example. Further, the controlling unit 160 is configured to associate three-dimensional image data generated by a medical image diagnosis apparatus with a three-dimensional space, on the basis of a registration between an arbitrary cross-sectional plane in the three-dimensional image data and a cross-sectional plane scanned by the ultrasound probe. The details of the process to associate the three-dimensional image data with the three-dimensional space will be explained later.

The internal storage unit 170 is configured to store therein various types of data such a control program to realize ultrasound transmissions and receptions, image processing, and display processing, as well as diagnosis information (e.g., subjects' IDs, medical doctors' observations) and diagnosis protocols. Further, the internal storage unit 170 may be used, as necessary, for storing therein any of the images stored in the image memory 150. Further, the internal storage unit 170 is configured to store therein volume data in another imaging modality obtained under the control of the controlling unit 160. Further, the internal storage unit 170 is configured to store therein various types of information used in processes performed by the controlling unit 160. The various types of information will be explained later.

The interface unit 180 is an interface configured to control exchanges of various types of information among the input device 12, the position information obtaining device 14, the network, and the apparatus main body 100. For example, the interface unit 180 controls the transfer of the position information obtained by the position information obtaining device 14 to the controlling unit 160.

An overall configuration of the ultrasound diagnosis apparatus according to the first embodiment has thus been explained. The ultrasound diagnosis apparatus 1 according to the first embodiment configured as described above is arranged to be able to improve the efficiency of the diagnosis process by eliminating the need to perform a registration even if the transmitter has moved, as a result of the processes performed by the position information obtaining device 14 and the controlling unit 160 explained in details below.

Figure 2A:
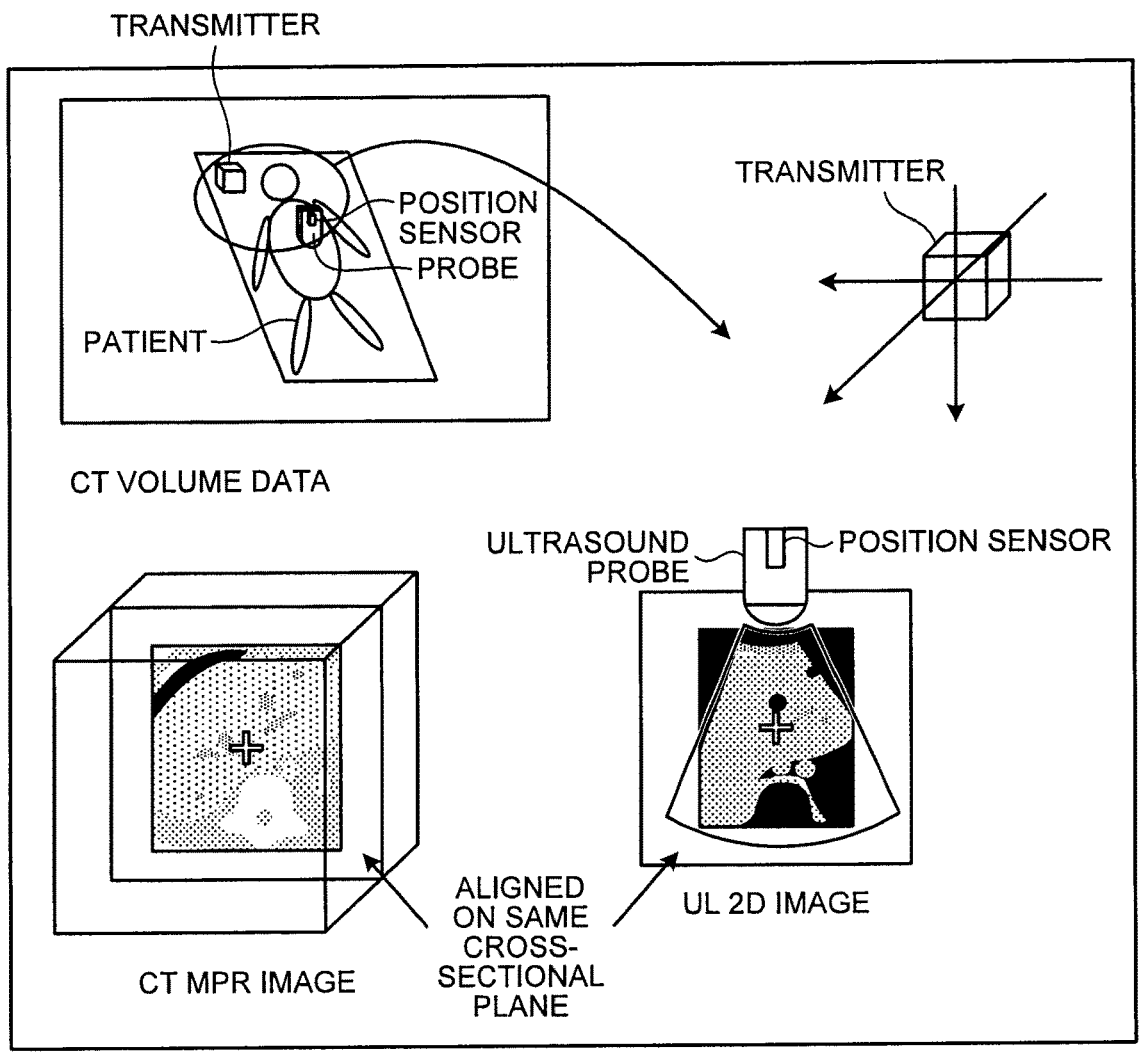
FIG. 2A is a drawing for explaining an example of a registration between images according to the first embodiment.
Figure 2B:
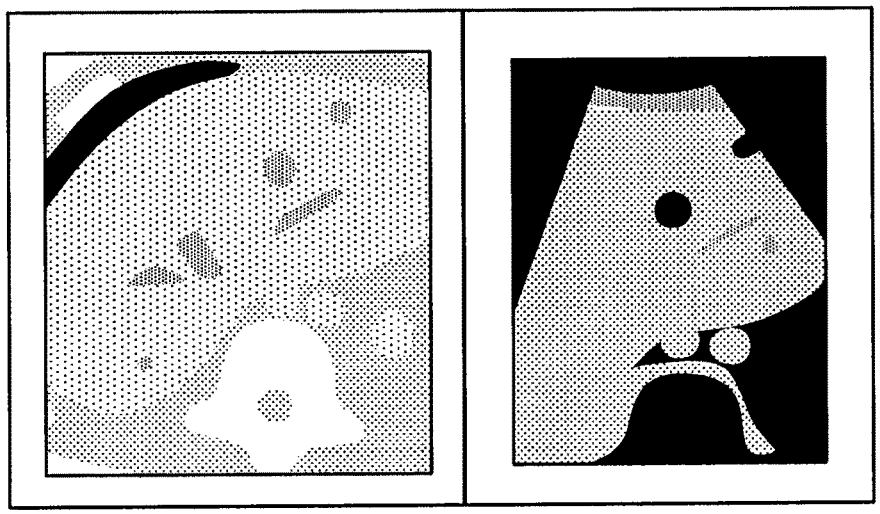
FIG. 2B is a drawing of an example of displaying positionally-aligned images side by side according to the first embodiment.

Next, a registration between images will be explained first with reference to FIGS. 2A and 2B, in a situation where a diagnosis process is performed by using a CT image or an MRI image as a reference image. FIG. 2A is a drawing for explaining an example of the registration between images according to the first embodiment. FIG. 2B is a drawing of an example of displaying positionally-aligned images side by side according to the first embodiment. In this situation, FIGS. 2A and 2B illustrate an example in which an MPR image (hereinafter, a "CT image") generated from volume data acquired by an X-ray CT apparatus is used as an image in another imaging modality. For example, when a diagnosis process or a treatment is performed by using a CT image as a reference image, the volume data acquired by the X-ray CT apparatus is associated with an ultrasound image, by using a sensor attached to an ultrasound probe, as shown in FIG. 2A.

For example, when a magnetic sensor is used, the three axes (X, Y, Z) of the ultrasound probe 11, to which the magnetic sensor is attached, within a three-dimensional magnetic field formed by a transmitter is aligned with the three axes of the volume data (called an "axis aligning process"). In an example, the ultrasound probe to which the magnetic sensor is attached is perpendicularly placed on the subject, and a setting button is pressed in that state, so as to set the orientation of the magnetic sensor at that time as the vertical direction.

Subsequently, the ultrasound probe 11 is moved so that a characteristic part that is the same as the characteristic part rendered in the CT image is rendered in the ultrasound image, and the position (the coordinates) of the magnetic sensor at that time is associated with a position (coordinates) in the volume data by pressing the setting button again. The characteristic part may be, for example, a blood vessel or the xiphisternum.

By associating the orientation and the coordinates of the magnetic sensor with the coordinates in the volume data in the other imaging modality as described above, it becomes possible for the ultrasound probe 11 to generate a two-dimensional image taken in substantially same position as the current scanned plane, from the volume data in the other imaging modality. For example, as shown in FIG. 2B, it becomes possible to display an MPR image (the image shown on the left) taken on the same cross-sectional plane as that of the ultrasound image (the image shown on the right), which changes as the ultrasound probe moves. Further, for example, by rendering and registering a lesion exhibiting a possibility of cancer detected from an image in the other imaging modality as a tumor region (a Region Of Interest [ROI]) in the MPR image, it is possible to append a mark within the ultrasound image taken in substantially the same position. In another example, by rendering an ROI in the ultrasound image, it is possible to append a mark in substantially the same position within the MPR image. As a result, a medical doctor is able to perform a puncture process according to the marks appended to the ultrasound image and the MPR image, while visually comparing these images with each other, the two images having mutually-different characteristics as images.

However, the technique described above is based on the premise that the transmitter forming the three-dimensional space used for defining the position of the position sensor is not moved. In other words, if the transmitter moves after the registration is performed to associate the position (the coordinates) of the magnetic sensor with the position (the coordinates) in the volume data, a misregistration occurs between the two positions. FIG. 3 is a drawing for explaining the problem with the conventional technique. FIG. 3 illustrates an example in which the transmitter moves on an X-Y plane.

For example, as shown in FIG. 3(A), let us discuss a situation where coordinates $(X_1, Y_1)$ of the position sensor in a space formed by the transmitter have been positionally aligned with coordinates $(X'_1, Y'_1)$ in the volume data acquired by an X-ray CT apparatus. As a result, as shown in FIG. 3(A), an MPR image taken in substantially the same position as the scanned plane of the ultrasound probe is generated from the volume data.

In this situation, for example, as shown in FIG. 3(B), if the transmitter moves on the X-Y plane, the three-dimensional space formed by the transmitter is shifted. Thus, the coordinates of the ultrasound probe (the position sensor) in the three-dimensional space change to $(X_2, Y_2)$, although the position of the ultrasound probe in the real space is the same as the position shown in FIG. 3(A) (i.e., the ultrasound probe has not moved). As a result of this misregistration, the MPR image generated from the volume data turns out to be, unfortunately, an image containing coordinates $(X'_2, Y'_2)$ that correspond to $(X_2, Y_2)$. It means that the MPR image taken in a position different from the plane that is actually scanned by the ultrasound probe is displayed.

Consequently, according to the conventional technique, it is necessary to perform the registration described above every time the transmitter has moved, and the efficiency of the diagnosis process is lowered. For example, when a medical examination or a treatment is performed by using the technique described above, the user may, in some situations, change the position of the transmitter after the medical examination or the treatment is started, for the purpose of improving the level of precision. More specifically, the strength of the magnetic field transmitted by the transmitter becomes weaker, as the distance from the transmitter becomes longer. Thus, the level of precision in the position detecting process of the ultrasound probe 11 becomes lower, as the distance of the magnetic sensor attached to the ultrasound probe 11 from the transmitter becomes longer.

To cope with this situation, when the distance between a diagnosed site and the transmitter is long, it is desirable to perform an image taking process by arranging the transmitter to be positioned near the diagnosed site in advance, so that the ultrasound probe 11 (the diagnosed site) and the transmitter are positioned close to each other. Alternatively, if the poles of a bed on which the subject is placed are made of metal, the poles can disturb the magnetic field. Thus, it is desirable to perform an image taking process after arranging the transmitter to be in a position distant from the poles. In these situations, according to the conventional technique, it is necessary to perform the registration every time the transmitter is moved. To cope with this issue, the ultrasound diagnosis apparatus 1 according to the first embodiment is configured to be able to improve the efficiency of a diagnosis process that is performed while a reference image is being referred to, by eliminating the registration required by moves of the transmitter.

Figure 4:
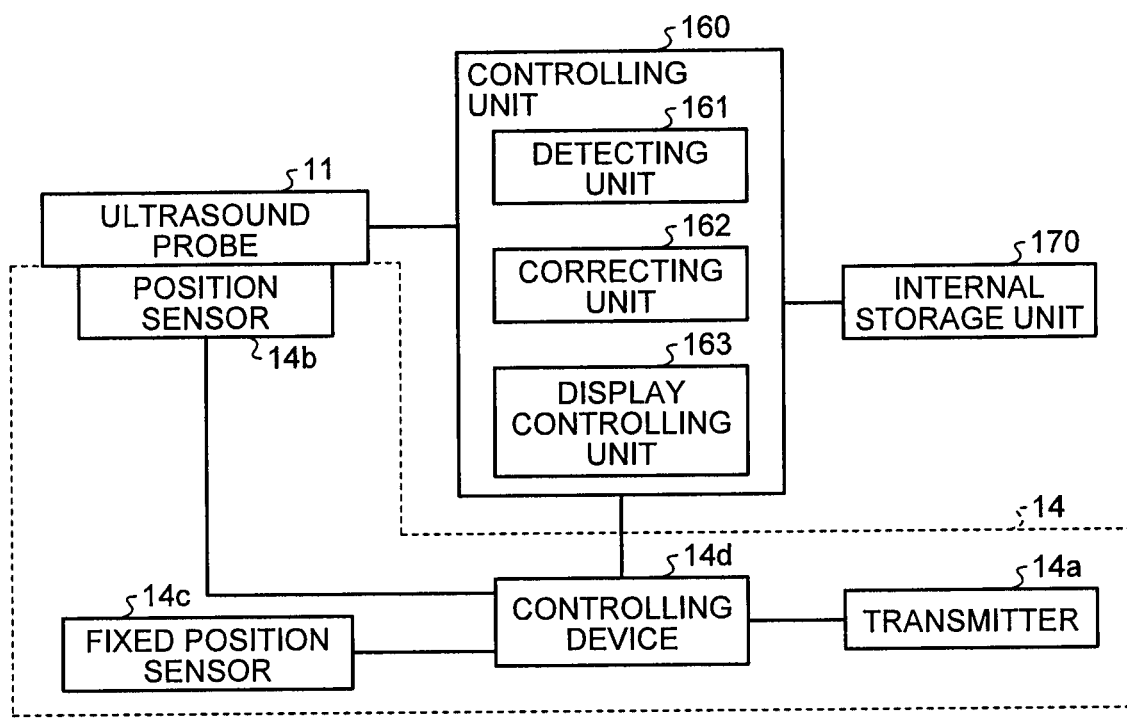
FIG. 4 is a drawing for explaining exemplary configurations of a position information obtaining device and a controlling unit according to the first embodiment.

Next, processes performed by the position information obtaining device 14 and the controlling unit 160 according to the first embodiment will be explained with reference to FIG. 4 and so on. FIG. 4 is a drawing for explaining exemplary configurations of the position information obtaining device 14 and the controlling unit 160 according to the first embodiment. The position information obtaining device 14 according to the first embodiment includes, as shown in FIG. 4, a transmitter 14a, a position sensor 14b, a fixed position sensor 14c, and a controlling device 14d. The position information obtaining device 14 is connected to the controlling unit 160 via the interface unit 180 (not shown).

The transmitter 14a is configured to transmit a reference signal. More specifically, the transmitter 14a is disposed in an arbitrary position and is configured to form a magnetic field that is centered on the transmitter 14a and extends outwardly. The position sensor 14b is configured to obtain position information in a three-dimensional space, by receiving the reference signal. More specifically, the position sensor 14b is attached to the surface of the ultrasound probe 11 and is configured to detect the three-dimensional magnetic field formed by the transmitter 14a, to convert information about the detected magnetic field into a signal, and to output the signal to the controlling device 14d.

The fixed position sensor 14c is configured to obtain position information in the three-dimensional space by receiving the reference signal. More specifically, the fixed position sensor 14c is configured to detect the three-dimensional magnetic field formed by the transmitter 14a, to convert information about the detected magnetic field into a signal, and to output the signal to the controlling device 14d. In this situation, the fixed position sensor 14c is fixed in an arbitrary position within the three-dimensional magnetic field. For example, the fixed position sensor 14c may be placed in the magnetic field by using a non-metallic arm extending from the bed on which the subject is lying. Alternatively, the fixed position sensor 14c may be disposed on the ultrasound diagnosis apparatus 1. In that situation, for example, the fixed position sensor 14c may be provided on an immobile part of an arm with which the ultrasound diagnosis apparatus 1 is provided and which is configured to support the transmitter 14a. Alternatively, of the ultrasound diagnosis apparatus 1, the fixed position sensor 14c may be disposed in a non-magnetic and non-metallic part within the magnetic field. Alternatively, if the transmitter 14a is supported by a pole, the fixed position sensor 14c may be disposed in an immobile part of the pole, such as a supporting pillar of the pole.

Further, the fixed position sensor 14c may be disposed on the subject. For example, of the subject undergoing a diagnosis process, the fixed position sensor 14c may be disposed in a predetermined part that does not move. In that situation, because the position of the fixed position sensor 14c with respect to the subject is supposed to be fixed, even if the subject has moved, it is possible to calculate a moving amount of the subject on the basis of an amount of change in the coordinates of the fixed position sensor 14c and to correct, for example, the association between the volume data and the ultrasound image by using the calculated moving amount. As described above, it is possible to dispose the fixed position sensor 14c in various positions. Thus, the fixed position sensor 14c is suitable for various situations as the occasion demands.

The controlling device 14d is configured to, on the basis of the signals received from the position sensor 14b and the fixed position sensor 14c, calculate the coordinates and the orientations of the position sensor 14b and the fixed position sensor 14c in a space of which the origin is the transmitter 14a and to output the calculated coordinates and orientations to the controlling unit 160. A diagnosis process is performed on the subject P in such a magnetic field area where the position sensor 14b attached to the ultrasound probe 11 is able to accurately detect the magnetic field of the transmitter 14a.

The controlling unit 160 includes a detecting unit 161, a correcting unit 162, and a display controlling unit 163 and is connected to the position information obtaining device 14 and to the internal storage unit 170 via a bus or the interface unit 180 (not shown).

The internal storage unit 170 is configured to store therein information about the coordinates of the fixed position sensor 14c within the magnetic field formed by the transmitter 14a. More specifically, the internal storage unit 170 stores therein the coordinates of the fixed position sensor 14c that are obtained and put therein by the detecting unit 161.

The detecting unit 161 is configured to, on the basis of the position information obtained by the fixed position sensor 14c, detect if the position of the transmitter has changed within the associated three-dimensional space. In other words, the detecting unit 161 detects if the position of the transmitter 14a has changed, while a cross-sectional plane in a medical image generated from three-dimensional image data generated by a medical image diagnosis apparatus is positionally aligned with the cross-sectional plane scanned by the ultrasound probe 11, by associating the three-dimensional image data with the three-dimensional space generated by the transmitter 14a. More specifically, the detecting unit 161 detects a change, if any, in the position of the transmitter 14a, by detecting a change in the coordinates of the fixed position sensor 14c that is fixed in the arbitrary position within the three-dimensional space generated by the transmitter 14a.

Even more specifically, when the volume data acquired in another imaging modality has positionally been aligned with the scanned plane of the ultrasound probe 11, the detecting unit 161 first obtains the coordinates (hereinafter, "initial coordinates") of the fixed position sensor 14c within the magnetic field formed by the transmitter 14a from the controlling device 14d and stores the obtained initial coordinates into the internal storage unit 170. After that, the detecting unit 161 obtains the coordinates of the fixed position sensor 14c, which are obtained with predetermined timing, and calculates an amount of change (hereinafter, a "change amount") from the initial coordinates stored in the internal storage unit 170.

In this situation, if the calculated change amount exceeds a predetermined threshold value, the detecting unit 161 determines that the position of the transmitter 14a has changed. On the contrary, if the calculated change amount does not exceed the predetermined threshold value, the detecting unit 161 determines that the position of the transmitter 14a has not changed. In other words, the detecting unit 161 according to the first embodiment detects the change in the coordinates of the fixed position sensor 14c that is fixed in the magnetic field formed by the transmitter 14a, as the change in the position of the transmitter 14a.

The threshold value described above used for judging whether the position of the transmitter 14a has changed or not may arbitrarily be set by an operator or a designer. For example, the threshold value may be set in accordance with the level of precision in the acquisition of the coordinates of the fixed position sensor 14c. Generally speaking, because position information detected by magnetic sensors fluctuates, it is desirable to set the threshold value while taking such fluctuations into consideration.

The correcting unit 162 is configured to, if a change in the position of the transmitter has been detected, correct a misregistration between the cross-sectional plane in the medical image (e.g., a cross-sectional plane in three-dimensional image data generated by a medical image diagnosis apparatus) and the cross-sectional plane scanned by the ultrasound probe 11, on the basis of the change amount of the position of the transmitter 14a. More specifically, the correcting unit 162 corrects the misregistration between the cross-sectional plane in the medical image and the cross-sectional plane scanned by the ultrasound probe 11, by transforming the coordinates of the position sensor 14b that is attached to the ultrasound probe 11 and is used for registration, on the basis of the change amount of the coordinates of the fixed position sensor 14c. In another example, the correcting unit 162 corrects the misregistration between the cross-sectional plane in the medical image and the cross-sectional plane scanned by the ultrasound probe 11, by correcting the association between the three-dimensional image data and the three-dimensional space on the basis of the change amount of the coordinates of the fixed position sensor 14c.

As explained above, the correcting unit 162 according to the first embodiment performs: a first correcting process to correct the misregistration, by performing the coordinate transformation on the obtained coordinates on the basis of the change amount calculated by the detecting unit 161, every time the coordinates of the position sensor 14b are obtained by the controlling device 14d; and a second correcting process to correct the misregistration by performing the coordinate transformation on the coordinates in the volume data, on the basis of the change amount calculated by the detecting unit 161.

Next, examples of the first correcting process and the second correcting process performed by the correcting unit 162 according to the first embodiment will be explained, with reference to FIGS. 5 and 6. FIG. 5 is a drawing for explaining an example of the first correcting process according to the first embodiment. FIG. 6 is a drawing for explaining an example of the second correcting process according to the first embodiment. FIGS. 5 and 6 illustrate examples in which the position of the transmitter 14a on an X-Y plane changes.

First, an example of the first correcting process will be explained. In the present example, let us discuss a situation where, for instance, as shown in FIG. 5(A), the coordinates $(X_1, Y_1)$ of the position sensor 14b in a space formed by the transmitter 14a have been positionally aligned with the coordinates $(X'_1, Y'_1)$ in the volume data acquired by an X-ray CT apparatus. As a result, an MPR image taken in substantially the same position as the scanned plane of the ultrasound probe 11 is generated from the volume data.

In this situation, the ultrasound diagnosis apparatus 1 according to the first embodiment is configured so that the fixed position sensor 14c is fixed in the magnetic field, as mentioned above, and coordinates $(X_3, Y_3)$ of the fixed position sensor 14c are obtained, as shown in FIG. 5(A). The detecting unit 161 obtains the coordinates $(X_3, Y_3)$ of the fixed position sensor 14c at the time when the coordinates $(X_1, Y_1)$ of the position sensor 14b are positionally aligned with the coordinates $(X'_1, Y'_1)$ in the volume data and stores the obtained coordinates $(X_3, Y_3)$ into the internal storage unit 170.

Further, as shown in FIG. 5(B), for example, if the position of the transmitter 14a has changed on an X-Y plane, the three-dimensional space formed by the transmitter 14a is shifted. Thus, the coordinates $(X_1, Y_1)$ of the position sensor 14b change to $(X_2, Y_2)$. In this situation, according to the first embodiment, as shown in FIG. 5(A), the coordinates $(X_3, Y_3)$ of the fixed position sensor 14c also change to $(X_4, Y_4)$. The detecting unit 161 obtains the coordinates $(X_4, Y_4)$ of the fixed position sensor 14c and calculates a change amount from the initial coordinates $(X_3, Y_3)$ of the fixed position sensor stored in the internal storage unit 170. In this situation, if the calculated change amount exceeds the predetermined threshold value, the detecting unit 161 determines that the position of the transmitter 14a has changed.

After that, when the detecting unit 161 has determined that the position of the transmitter 14a has changed, the correcting unit 162 corrects the misregistration by using the change amount calculated by the detecting unit 161. In other words, as shown in FIG. 5(B), the correcting unit 162 transforms the coordinates of the position sensor 14b to $(X_1, Y_1)$, by multiplying the coordinates $(X_2, Y_2)$ of the position sensor 14b by a transformation coefficient "$M_1$" used for transforming the coordinates $(X_4, Y_4)$ of the fixed position sensor 14c into the initial coordinates $(X_3, Y_3)$. As a result, it is possible to change the coordinates of the position sensor 14b obtained after the positional change of the transmitter 14a, back to the coordinates prior to the positional change of the transmitter 14a. It is therefore possible to generate, from the volume data, an MPR image taken substantially in the same position as the scanned plane of the ultrasound probe 11.

Next, an example of the second correcting process will be explained. In the present example, similarly to the first correcting process, a change in the position of the transmitter 14a is detected by the detecting unit 161. After that, the correcting unit 162 corrects the misregistration by using the change amount calculated by the detecting unit 161. For example, as shown in FIG. 6(A), let us discuss a situation where, as shown in FIG. 6(A), the coordinates $(X_1, Y_1)$ of the position sensor 14b in the space formed by the transmitter 14a are positionally aligned with the coordinates $(X'_1, Y'_1)$ in the volume data acquired by an X-ray CT apparatus, so that the coordinates $(X_3, Y_3)$ of the fixed position sensor 14c are obtained.

Subsequently, after the position of the transmitter 14a has changed in the same manner as shown in FIG. 5, the correcting unit 162 calculates, as shown in FIG. 6(B), the coordinates $(X_2, Y_2)$, by multiplying the coordinates $(X_1, Y_1)$ of the position sensor 14b by a transformation coefficient "$M_2$" used for transforming the initial coordinates $(X_3, Y_3)$ of the fixed position sensor 14c into coordinates $(X_4, Y_4)$. After that, the correcting unit 162 positionally aligns, again, the calculated coordinates $(X_2, Y_2)$ with the coordinates $(X'_1, Y'_1)$ in the volume data. As a result, it is possible to associate again the coordinates in the magnetic field after the positional change of the transmitter 14a with the volume data. In other words, in the second correcting process, there is no need to perform the correcting process every time the coordinates of the position sensor 14b are obtained. It is therefore possible to inhibit the processing load from increasing.

Returning to the description of FIG. 4, the display controlling unit 163 is configured to display a two-dimensional image (e.g., an MPR image) generated from volume data in another imaging modality, side by side with an ultrasound image on the monitor 13. For example, the display controlling unit 163 displays an MPR image taken in substantially the same position as the scanned plane of the ultrasound probe 11 side by side on the monitor 13.

Further, when the detecting unit 161 has determined that the position of the transmitter 14a changed, the display controlling unit 163 displays a message on the monitor 13. For example, the display controlling unit 163 displays a warning message "the transmitter has moved" on the monitor 13. As another example, the display controlling unit 163 displays a message "the misregistration due to the move of the transmitter has been corrected" on the monitor 13.

As yet another example, the display controlling unit 163 displays, on the monitor 13, a message "Please adjust the position of the transmitter" for the user, together with the warning message "the transmitter has moved". After that, when the user has put the transmitter 14a back to the correct position, the display controlling unit 163 displays a message "the transmitter has returned to the normal position" on the monitor 13. In this situation, the display controlling unit 163 may also display, on the monitor 13, a matching ratio between the original position and the position to which the user has moved the transmitter 14a (an index indicating the extent by which the transmitter 14a has returned to the correct position). With this arrangement, the user is able to manually move the transmitter 14a while checking the matching ratio and is therefore able to return the transmitter 14a to a more accurate position. The matching ratio displayed by the display controlling unit 163 may be expressed with a numerical value (%). Alternatively, the matching ratio displayed by the display controlling unit 163 may be displayed as a chart on an X-Y plane of which the origin corresponds the original position (the position used in the registration) of the transmitter 14a and in which the current position of the transmitter 14a is plotted. In that situation, the user can move the transmitter 14a in such a manner that the plotted point overlaps with the origin. Alternatively, it is also acceptable to display a bar expressing the X-axis and another bar expressing the Y-axis, so as to display the moving amount of the transmitter in each of the axial directions. In other words, the user can move the transmitter in the X-axis and Y-axis directions while checking the bars.

Figure 7:
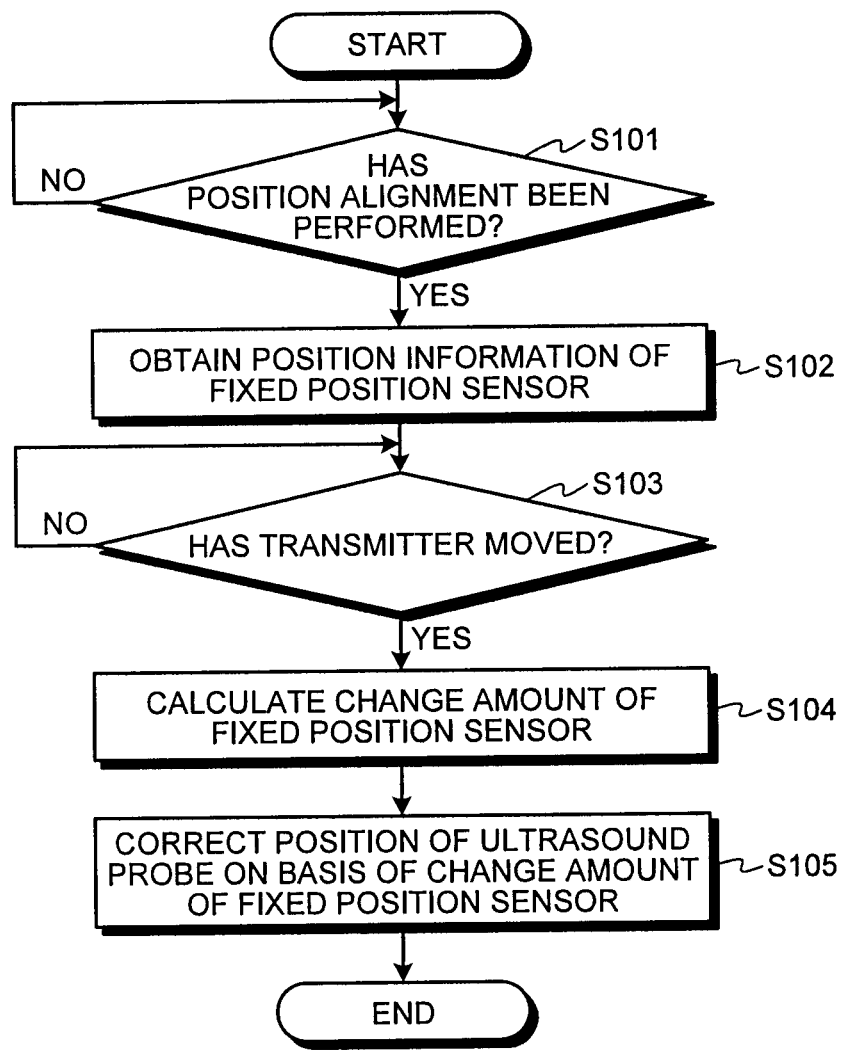
FIG. 7 is a flowchart of a procedure in a process performed by the ultrasound diagnosis apparatus according to the first embodiment.

Next, a process performed by the ultrasound diagnosis apparatus 1 according to the first embodiment will be explained. FIG. 7 is a flowchart of a procedure in the process performed by the ultrasound diagnosis apparatus 1 according to the first embodiment. FIG. 7 illustrates the process performed in a situation where the position sensor 14b and the fixed position sensor 14c are positioned in a magnetic field area that permits an accurate detection of the magnetic field of the transmitter 14a.

As shown in FIG. 7, the ultrasound diagnosis apparatus 1 according to the first embodiment is configured so that, when coordinates in the volume data are positionally aligned with coordinates in the magnetic field (step S101: Yes), the detecting unit 161 obtains the position information (the coordinates in the magnetic field) of the fixed position sensor 14c (step S102) and stores the obtained position information into the internal storage unit 170.

After that, the position information obtaining device 14 obtains position information of the fixed position sensor 14c with predetermined timing. In this situation, the timing with which the position information of the fixed position sensor 14c is obtained may arbitrarily set. For example, it is acceptable to configure the timing so that the position information of the fixed position sensor 14c is constantly obtained while a scan is being performed. Alternatively, it is also acceptable to configure the timing so that the position information obtaining process is suspended when a freeze button has been pressed and so that the position information is obtained when the freeze is cancelled. Alternatively, another arrangement is also acceptable in which a correction mode is turned on and off by operations performed on a button, so that the position information is constantly obtained while the correction mode is on.

When the position information of the fixed position sensor 14c has been obtained with the timing described above, the detecting unit 161 judges whether the transmitter 14a has moved or not (step S103). In this situation, when having determined that the transmitter 14a has moved (step S103: Yes), the detecting unit 161 calculates a change amount of the coordinates of the fixed position sensor 14c (step S104). After that, the correcting unit 162 corrects the position of the ultrasound probe 11 (i.e., the coordinates obtained by the position sensor 1b), on the basis of the change amount of the fixed position sensor 14c (step S105).

On the contrary, when having determined that the transmitter 14a has not moved (step S103: No), the detecting unit 161 continues to judge whether the transmitter 14a has moved (step S103). The procedure in the process described above refers to the example where the first correcting process is performed. When the second correcting process is performed, the association between coordinates in the volume data and coordinates in the magnetic field is corrected at step S105, on the basis of the change amount of the position of the fixed position sensor 14c.

As explained above, according to the first embodiment, the transmitter 14a transmits the reference signal. The position sensor 14b and the fixed position sensor 14c obtain the position information in the three-dimensional space, by receiving the reference signal. The controlling unit 160 associates the three-dimensional image data generated by the medical image diagnosis apparatus with the three-dimensional space, on the basis of the registration between the arbitrary cross-sectional plane in the three-dimensional image data and the cross-sectional plane scanned by the ultrasound probe 11. On the basis of the position information obtained by the fixed position sensor 14c, the detecting unit 161 detects if the position of the transmitter 14a has changed within the associated three-dimensional space. When a change in the position of the transmitter 14a has been detected, the correcting unit 162 corrects the misregistration between the cross-sectional plane in the medical image and the cross-sectional plane scanned by the ultrasound probe 11, on the basis of the change amount of the position of the transmitter 14a. Accordingly, the ultrasound diagnosis apparatus 1 according to the first embodiment is able to eliminate the registration required by the moves of the transmitter and thus makes it possible to improve the efficiency of the diagnosis process that is performed while the reference image is being referred to.

Further, according to the first embodiment, the detecting unit 161 detects the change in the position of the transmitter 14a, by detecting the change in the coordinates of the fixed position sensor 14c fixed in the arbitrary position within the three-dimensional space generated by the transmitter 14a. Further, the correcting unit 162 corrects the misregistration between the cross-sectional plane in the medical image and the cross-sectional plane scanned by the ultrasound probe 11, by transforming the coordinates of the position sensor 14b that is attached to the ultrasound probe 11 and is used for registration, on the basis of the change amount of the coordinates of the fixed position sensor 14c. Consequently, with the simple configuration employing the fixed position sensor 14c, the ultrasound diagnosis apparatus 1 according to the first embodiment makes it possible to eliminate the registration required by the moves of the transmitter 14a.

Further, according to the first embodiment, the correcting unit 162 corrects the misregistration between the cross-sectional plane in the medical image and the cross-sectional plane scanned by the ultrasound probe 11, by correcting the association between volume data and the three-dimensional space, on the basis of the change amount of the coordinates of the fixed position sensor 14c. Consequently, the ultrasound diagnosis apparatus 1 according to the first embodiment makes it possible to generate, from the volume data, the two-dimensional image taken in substantially the same position as the scanned plane of the ultrasound probe 11, without the need to correct the coordinates of the position sensor 14b every time. As a result, the ultrasound diagnosis apparatus 1 according to the first embodiment makes it possible to reduce the processing load.

Figure 8:
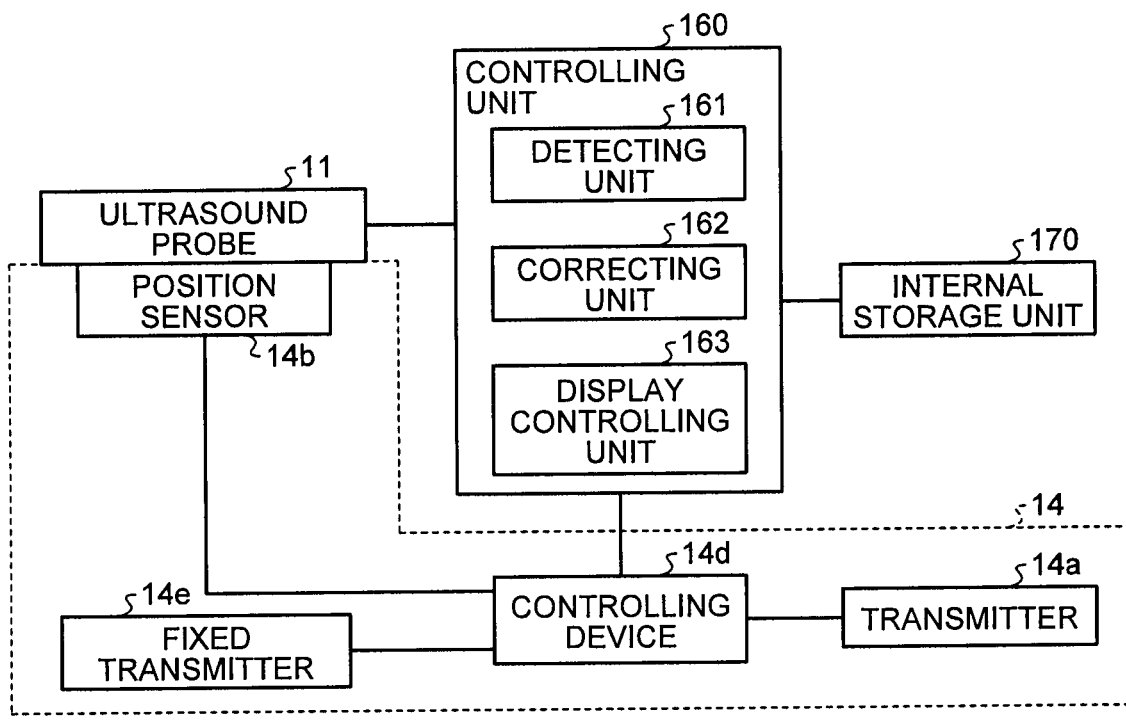
FIG. 8 is a drawing for explaining exemplary configurations of a position information obtaining device and a controlling unit according to a second embodiment.

In the first embodiment described above, the example is explained in which the change in the position of the transmitter 14a is detected by using the fixed position sensor 14c. In a second embodiment, an example will be explained in which a change in the position of the transmitter 14a is detected by using a fixed transmitter. FIG. 8 is a drawing for explaining exemplary configurations of the position information obtaining device 14 and the controlling unit 160 according to the second embodiment. The position information obtaining device 14 and the controlling unit 160 according to the second embodiment are different from the position information obtaining device 14 and the controlling unit 160 according to the first embodiment in that the fixed position sensor 14c is omitted and that a fixed transmitter 14e is newly provided, and in the specifics of the processes performed by the detecting unit 161. In the following sections, the second embodiment will be explained while a focused is placed on these differences.

The fixed transmitter 14e is disposed in an arbitrary position and is configured to form a magnetic field that is centered on the fixed transmitter 14e and extends outwardly. More specifically, the fixed transmitter 14e is disposed in such a position that the magnetic field is formed in the position scanned by the ultrasound probe 11. In this situation, the fixed transmitter 14e forms the magnetic field so that the magnetic field formed thereby does not interfere with the magnetic field formed by the transmitter 14a. For example, the fixed transmitter 14e generates the magnetic field while staggering the timing with which the magnetic field is generated or while varying the transmission frequency, so that the magnetic field generated thereby does not overlap with the magnetic field formed by the transmitter 14a. This type of control is arbitrarily set by an operator or a designer and is executed by the controlling device 14d.

The detecting unit 161 according to the second embodiment is configured to detect a change in the correspondence relationship between the coordinates of the position sensor 14b within a three-dimensional space generated by the transmitter 14a and the coordinates of the position sensor 14b in a three-dimensional space generated by the fixed transmitter 14e that is different from the transmitter 14a and is used for correcting purposes, the position sensor 14b being attached to the ultrasound probe 11 and used for registration.

More specifically, when volume data acquired in an another imaging modality has been positionally aligned with the scanned plane of the ultrasound probe 11, the detecting unit 161 first obtains the coordinates of the position sensor 14b in the magnetic field formed by the transmitter 14a and the coordinates of the position sensor 14b in the magnetic field formed by the fixed transmitter 14e, from the controlling device 14d, and calculates the correspondence relationship between the two sets of coordinates. For example, the detecting unit 161 calculates the distance between the two sets of coordinates or the like and stores the calculated distance into the internal storage unit 170. After that, the detecting unit 161 obtains two sets of coordinates of the position sensor 14b obtained with predetermined timing, calculates the distance between the two sets of coordinates, and further calculates a change amount from the distance stored in the internal storage unit 170.

In this situation, if the calculated change amount exceeds a predetermined threshold value, the detecting unit 161 determines that the position of the transmitter 14a has changed. On the contrary, if the calculated change amount does not exceed the predetermined threshold value, the detecting unit 161 determines that the position of the transmitter 14a has not changed. In other words, the detecting unit 161 according to the second embodiment detects the change in the positional relationship between the coordinates of the position sensor 14b in the magnetic field formed by the transmitter 14a and the coordinates of the position sensor 14b in the magnetic field formed by the fixed transmitter 14e, as the change in the position of the transmitter 14a.

The threshold value described above used for judging whether the position of the transmitter 14a has changed or not may arbitrarily be set by an operator or a designer. For example, the threshold value may be set in accordance with the level of precision in the acquisition of the coordinates of the position sensor 14b.

The correcting unit 162 according to the second embodiment is configured to, when the detecting unit 161 has determined that the position of the transmitter 14a has changed, correct a misregistration between a cross-sectional plane in a medical image and the cross-sectional plane scanned by the ultrasound probe 11, by correcting the association between the volume data and the three-dimensional space, on the basis of the change amount of the correspondence relationship calculated by the detecting unit 161.

For example, the correcting unit 162 corrects the misregistration by transforming the coordinates in the magnetic field formed by the transmitter 14a, so that the distance between the two sets of coordinates calculated by the detecting unit 161 becomes equal to the distance stored in the internal storage unit 170.

Figure 9:
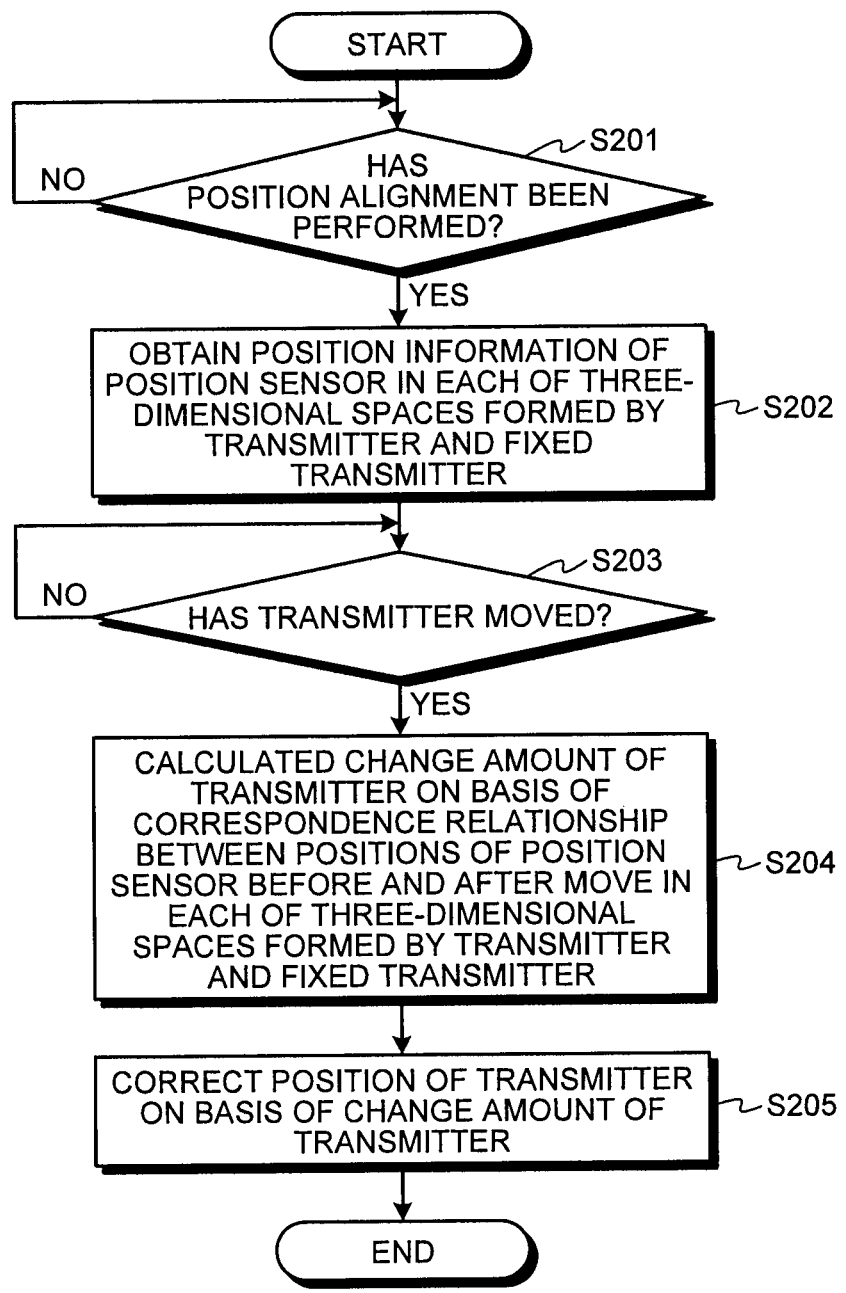
FIG. 9 is a flowchart of a procedure in a process performed by an ultrasound diagnosis apparatus according to the second embodiment.

Next, a procedure in a process performed by the ultrasound diagnosis apparatus 1 according to the second embodiment will be explained. FIG. 9 is a flowchart of the procedure in the process performed by the ultrasound diagnosis apparatus according to the second embodiment. FIG. 9 illustrates the process performed in a situation where the position sensor 14b is positioned in a magnetic field area that permits an accurate detection of the magnetic fields of the transmitter 14a and the fixed transmitter 14e.

As shown in FIG. 9, the ultrasound diagnosis apparatus 1 according to the second embodiment is configured so that, when coordinates in the volume data are positionally aligned with coordinates in the magnetic field (step S201: Yes), the detecting unit 161 obtains the position information (the coordinates) of the position sensor 14b in each of the three-dimensional spaces (the magnetic fields) formed by the transmitter 14a and the fixed transmitter 14e (step S202). After that, the detecting unit 161 stores the correspondence relationship between the two sets of coordinates into the internal storage unit 170.

Subsequently, with predetermined timing, the position information obtaining device 14 obtains the position information of the position sensor 14b in each of the magnetic fields formed by the transmitter 14a and the fixed transmitter 14e. In this situation, the timing with which the position information of the position sensor 14b is obtained may arbitrarily be set, like in the first embodiment.

When the position information of the position sensor 14b has been obtained with the timing described above, the detecting unit 161 judges whether the transmitter 14a has moved or not (step S203). In this situation, when having determined that the transmitter 14a has moved (step S203: Yes), the detecting unit 161 calculates a change amount of the transmitter 14a, on the basis of the correspondence relationship between the positions of the position sensor 14b before and after the move in each of the magnetic fields formed by the transmitter 14a and the fixed transmitter 14e (step S204). After that, the correcting unit 162 corrects the position of the transmitter 14a, on the basis of the change amount of the transmitter 14a (step S205).

On the contrary, when having determined that the transmitter 14a has not moved (step S203: No), the detecting unit 161 continues to judge whether the transmitter 14a has moved (step S203).

As explained above, according to the second embodiment, the detecting unit 161 detects the change in the position of the transmitter 14a, by detecting the change in the correspondence relationship between the coordinates of the position sensor 14b in the three-dimensional space generated by the transmitter 14a and the coordinates of the position sensor 14b in the three-dimensional space generated by the fixed transmitter 14e that is different from the transmitter 14a and is used for the correcting processes, the position sensor 14b being attached to the ultrasound probe 11 and used for the registration. Further, the correcting unit 162 corrects the misregistration between the cross-sectional plane in the medical image and the cross-sectional plane scanned by the ultrasound probe 11, by correcting the association between the volume data and the three-dimensional space, on the basis of the change amount of the correspondence relationship. Consequently, with the simple configuration employing the fixed transmitter 14e, the ultrasound diagnosis apparatus 1 according to the second embodiment makes it possible to eliminate the registration required by the moves of the transmitter 14a.

In the first and the second embodiments described above, the examples are explained in which the change in the position of the transmitter 14a is detected by using either the fixed position sensor 14c or the fixed transmitter 14e. In a third embodiment, an example will be explained in which a change in the position of the transmitter 14a is detected without additionally using the fixed position sensor 14c or the fixed transmitter 14e. Configurations of the position information obtaining device 14 and the controlling unit 160 according to the third embodiment can be obtained by omitting the fixed position sensor 14c from the configurations (see FIG. 4) of the position information obtaining device 14 and the controlling unit 160 according to the first embodiment. Thus, the drawing thereof will be omitted.

The ultrasound diagnosis apparatus 1 according to the third embodiment is configured by arranging the position sensor 14b to have the function of the fixed position sensor 14c according to the first embodiment. In other words, in the third embodiment, while the position sensor 14b is fixed in a magnetic field, the position of the transmitter 14a is changed, so that a correcting process is performed by using a change amount of the coordinates of the position sensor 14b. This method is usable in a situation where, for example, the operator changes the position of the transmitter after a medical examination or a treatment is started, for the purpose of improving the level of precision. For example, the input device 12 receives input operations indicating a start and an end of the change in the position of the transmitter 14a. After that, the detecting unit 161 calculates a change amount of the position of the transmitter 14a on the basis of the position information obtained by the position sensor 14b at the point in time when the input operation indicating the start of the change in the position of the transmitter 14a is received and the position information obtained by the position sensor 14b at the point in time when the input operation indicating the end of the change in the position of the transmitter 14a is received. After that, the correcting unit 162 corrects the misregistration on the basis of the change amount of the position of the transmitter 14a calculated by the detecting unit 161.

FIG. 10 is a drawing for explaining an example of the correcting process according to the third embodiment. FIG. 10 illustrates an example in which the position of the transmitter 14a on an X-Y plane changes. For example, as shown in FIG. 10(A), let us discuss a situation where the coordinates $(X_1, Y_1)$ of the position sensor 14b in a space formed by the transmitter 14a have been positionally aligned with the coordinates $(X'_1, Y'_1)$ in the volume data acquired by an X-ray CT apparatus. As a result, an MPR image taken in substantially the same position as the scanned plane of the ultrasound probe 11 is generated from the volume data.

In this situation, for example, if the operator desires to change the position of the transmitter 14a for the purpose of improving the level of precision, the operator presses a correction button included in the input device 12, for example. When the correction button has been pressed, for example, the display controlling unit 163 displays, on the monitor 13, a message "The transmitter will be moved. Please fix the ultrasound probe (the position sensor)", so as to prompt the operator to fix the ultrasound probe 11.

In this situation, for example, as shown in FIG. 10(A), the detecting unit 161 according to the third embodiment obtains the coordinates $(X_1, Y_1)$ of the position sensor 14b and stores the obtained coordinates $(X_1, Y_1)$ into the internal storage unit 170. When the coordinates $(X_1, Y_1)$ of the position sensor 14b have been stored, for example, the display controlling unit 163 displays a message "Please move the transmitter" on the monitor 13, so as to prompt the operator to move the transmitter 14a.

After that, for example, as shown in FIG. 10(B), the detecting unit 161 obtains the coordinates $(X_2, Y_2)$ of the position sensor 14b after the positional change of the transmitter 14a on an X-Y plane. In this situation, the detecting unit 161 calculates a change amount between the obtained coordinates $(X_2, Y_2)$ of the position sensor 14b and the coordinates $(X_1, Y_1)$ stored in the internal storage unit 170.

Subsequently, the correcting unit 162 according to the third embodiment corrects the misregistration by using the change amount calculated by the detecting unit 161. For example, as shown in FIG. 10(B), the correcting unit 162 calculates a transformation coefficient "M" used for transforming the coordinates $(X_1, Y_1)$ of the position sensor 14b into the coordinates $(X_2, Y_2)$. After that, the correcting unit 162 performs a correcting process by using the calculated transformation coefficient "M". With this arrangement, it is possible to associate again the coordinates in the magnetic field obtained after the positional change of the transmitter 14a with the volume data.

Next, a procedure in a process performed by the ultrasound diagnosis apparatus 1 according to the third embodiment will be explained. FIG. 11 is a flowchart of the procedure in the process performed by the ultrasound diagnosis apparatus 1 according to the third embodiment. FIG. 11 illustrates the process performed in a situation where the position sensor 14b is positioned in a magnetic field area that permits an accurate detection of the magnetic field of the transmitter 14a.

As shown in FIG. 11, the ultrasound diagnosis apparatus 1 according to the third embodiment is configured so that, when the correction button has been pressed (step S301: Yes), the display controlling unit 163 displays, on the monitor 13, a message that prompts fixing the ultrasound probe 11 (step S302). Subsequently, the detecting unit 161 obtains the position information (the coordinates) of the position sensor 14b prior to the move (step S303). After that, the detecting unit 161 stores the obtained coordinates into the internal storage unit 170.

Subsequently, the display controlling unit 163 displays a message that prompts moving the transmitter 14a on the monitor 13 (step S304). After that, the detecting unit 161 judges whether the correction end button has been pressed (step S305). If the correction end button has been pressed (step S305: Yes), the detecting unit 161 obtains the position information of the position sensor 14b after the move (step S306). Subsequently, the correcting unit 162 corrects the position of the ultrasound probe 11, on the basis of the change amount between the positions of the position sensor 14b before and after the move (step S307).

On the contrary, having determined that the correction end button has not been pressed (step S305: No), the detecting unit 161 continues to judge whether the correction end button has been pressed (step S305).

As explained above, in the third embodiment, the ultrasound diagnosis apparatus 1 according to the third embodiment performs the correcting process required by the move of the transmitter 14a, without using the fixed position sensor 14c or the fixed transmitter 14e. Consequently, the ultrasound diagnosis apparatus 1 according to the third embodiment makes it possible to improve the efficiency of the diagnosis process, by using the existing position information obtaining device.

The first, the second, and the third embodiments have thus been explained. The disclosure herein, however, may be carried out in various modes other than those described above in the first, the second, and the third embodiments.

(1) Detecting a Change in the Position of the Transmitter

In the first and the second embodiments described above, the examples are explained in which the change in the position of the transmitter 14a is detected by using the fixed position sensor 14c and the fixed transmitter 14e, respectively; however, possible embodiments are not limited to these examples. For instance, it is acceptable to detect a change in the position of the transmitter 14a by mechanically measuring a move of the arm portion that is configured to fix the transmitter 14a.

In that situation, for example, a gear is provided in a movable region of the arm fixing the transmitter, and a detecting device is provided so as to detect how much the gear has moved. Further, the detecting unit 161 obtains, from the detecting device, the move of the gear due to the move of the arm, so as to detect the obtained move of the gear as a change in the position of the transmitter 14a. On the basis of the moving amount of the gear, the correcting unit 162 corrects the misregistration between a cross-sectional plane in a medical image and the cross-sectional plane scanned by the ultrasound probe 11.

In another example, a change in the position of the transmitter 14a may be detected by performing an image processing process using one or more cameras. In that situation, the ultrasound diagnosis apparatus 1 further includes one or more cameras configured to take images of the transmitter 14a and a reference point. For example, a plurality of cameras may be provided so as to take images of the transmitter 14a and the reference point from a plurality of viewpoints. In this situation, any type of reference point may be used, as long as the reference point is fixed. Further, the detecting unit 161 identifies a relative positional relationship between the transmitter 14a and the reference point by performing an image recognition pattern matching process on the images taken by the cameras. After that, the detecting unit 161 detects a change in the position of the transmitter 14a, on the basis of a change in the identified correspondence relationship (e.g., the distance) between the transmitter 14a and the reference point.

The correcting unit 162 corrects the misregistration between a cross-sectional plane in a medical image and the cross-sectional plane scanned by the ultrasound probe 11, on the basis of the change amount of the correspondence relationship between the transmitter 14a and the reference point detected by the detecting unit 161.

(2) The Position Sensor

In the first, the second, and the third embodiments described above, the examples are explained in which the magnetic sensor is used as the position sensor; however, possible embodiments are not limited to these examples. For instance, it is also acceptable to use an infrared sensor.

(3) Targets of the Correcting Process

In the first, the second, and the third embodiments described above, the correcting processes that are performed when the transmitter 14a has moved two-dimensionally (i.e., on an X-Y plane) are explained; however, possible embodiments are not limited to these examples. For instance, it is possible to perform a correcting process in the same manner as described above, even when the transmitter 14a has moved three-dimensionally.

(4) Automatic Correcting Process

In the first, the second, and the third embodiments described above, the examples in which the transmitter 14a is moved manually are explained; however, possible embodiments are not limited to these examples. For instance, it is possible to perform a correcting process in the same manner even when the transmitter 14a is disposed on an arm that moves automatically. In that situation, an arrangement is also acceptable in which, when a change in the position of the transmitter 14a has been detected, control is exercised so as to automatically return the transmitter 14a to the original position.

(5) The Fixed Transmitter

In the second embodiment described above, the example is explained in which, of the two transmitters, one is the transmitter used for the registration with the volume data, whereas the other transmitter is used as the fixed transmitter; however, possible embodiments are not limited to this example. It is acceptable to interchange the transmitters in accordance with the levels of precision of the transmitters. For example, the detecting unit 161 may use the transmitter 14a and the fixed transmitter 14e while interchanging these transmitters on the basis of levels of precision of the three-dimensional spaces generated by the transmitter 14a and the fixed transmitter 14e.

In one example, the detecting unit 161 monitors distortions (e.g., quality values) in the magnetic fields generated by the transmitter 14a and the fixed transmitter 14e and, if the distortion in the magnetic field generated by the fixed transmitter 14e is smaller than the distortion in the magnetic field generated by the transmitter 14a, the detecting unit 161 uses the transmitters after interchanging the two transmitters. In other words, the detecting unit 161 obtains, from the controlling device 14d, the coordinates of the position sensor 14b in the magnetic field formed by the transmitter 14a and the coordinates of the position sensor 14b in the magnetic field formed by the fixed transmitter 14e and further calculates a correspondence relationship between the two sets of coordinates. After that, the detecting unit 161 obtains two sets of coordinates of the position sensor 14b obtained with predetermined timing and calculates the distance between the two sets of coordinates. If the calculated change amount exceeds a predetermined threshold value, the detecting unit 161 determines that the position of the fixed transmitter 14e has changed. On the contrary, if the calculated change amount does not exceed the predetermined threshold value, the detecting unit 161 determines that the position of the fixed transmitter 14e has not changed. In other words, the detecting unit 161 detects the change in the positional relationship between the coordinates of the position sensor 14b in the magnetic field formed by the transmitter 14a and the coordinates of the position sensor 14b in the magnetic field formed by the fixed transmitter 14e, as the change in the position of the fixed transmitter 14e.

Further, the correcting unit 162 corrects the misregistration in accordance with the change amount of the position of the fixed transmitter 14e detected by the detecting unit 161. When the transmitters are interchanged as described above, the correspondence relationship between the ultrasound image and the volume data while the transmitter 14a is used and the correspondence relationship between the ultrasound image and the volume data while the fixed transmitter 14e is used are stored, in advance, at the stage where the volume data acquired by the medical image diagnosis apparatus is positionally aligned with the ultrasound image. After that, the correcting unit 162 performs a correcting process on one of the correspondence relationships stored in advance. As a result, the ultrasound diagnosis apparatus 1 disclosed herein makes it possible to perform the registration and the correcting process more accurately.

Further, the transmitters may be interchanged as described above occasionally or may be interchanged when, for example, a freeze button has been pressed by the operator. In the latter situation, when the freeze button has been pressed by the operator, the detecting unit 161 compares distortions with each other that are in the magnetic fields generated by the transmitter 14a and the fixed transmitter 14e and interchanges the transmitters, so that the transmitter having the smaller distortion is used for the registration between the volume data and the ultrasound image. With this arrangement, the ultrasound diagnosis apparatus 1 disclosed herein is able to prevent the interchanges from occurring during diagnosis processes and thus makes it possible to interchange the transmitters in a smooth manner, while keeping the processing load small.

(6) The Fixed Position Sensor

In the first embodiment described above, the example in which the fixed position sensor 14c is additionally provided is explained; however, possible embodiments are not limited to this example. For instance, it is also acceptable to use a position sensor attached to an ultrasound probe that is not in operation as the fixed position sensor 14c. In that situation, for example, a first probe position sensor that serves as the position sensor 14b and a second probe position sensor that serves as the fixed position sensor 14c are used as position sensors. Further, for example, the detecting unit 161 detects a change in the position of the transmitter 14a, by detecting a change in the coordinates of the second probe position sensor attached to an ultrasound probe that is disposed in an arbitrary position within the three-dimensional space generated by the transmitter 14a and is not in operation. After that, the correcting unit 162 corrects the misregistration between a cross-sectional plane in the medical image and the cross-sectional plane scanned by the ultrasound probe 11, by transforming the coordinates of the first probe position sensor that is attached to the ultrasound probe 11 in operation and is used for registration, on the basis of the change amount of the coordinates of the second probe position sensor.

The correcting process using the second probe position sensor may be performed as the process to correct the misregistration by performing the coordinate transformation on the basis of the change amount as described above (i.e., the first correcting process in the first embodiment). Alternatively, the correcting process using the second probe position sensor may be performed as the process to correct the misregistration by performing the coordinate transformation on coordinates in the volume data on the basis of the change amount calculated by the detecting unit 161 (i.e., the second correcting process in the first embodiment). Further, when the second probe position sensor is used as described above, the ultrasound probe that is not in operation and to which the second probe position sensor is attached may be placed in a probe holder or may be placed in a predetermined fixing position. In either situation, the location in which the ultrasound probe is placed is a location within the magnetic field where no magnetic material or metal is positioned nearby.

When the ultrasound diagnosis apparatus according to at least one aspect of the exemplary embodiments is used, it is possible to eliminate the need to perform the registration even if the transmitter has moved, and it is therefore possible to improve the efficiency of the diagnosis process.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
   a first position sensor configured to obtain position information in a three-dimensional space by receiving a reference signal from a transmitter;
   a second position sensor fixed at an arbitrary position within the three-dimensional space and configured to obtain position information in the three-dimensional space by receiving the reference signal from the transmitter; and
   processing circuitry configured to
      associate three-dimensional image data generated by a medical image diagnosis apparatus with the three-dimensional space, on a basis of a registration between image data generated by the medical image diagnosis apparatus and image data scanned by an ultrasound probe attached with the first position sensor,
      detect movement of the transmitter within the associated three-dimensional space, on a basis of the position information obtained by the second position sensor, and
      correct a misregistration between a cross-sectional plane in the three-dimensional image data and a cross-sectional plane scanned by the ultrasound probe, by correcting a transformation coefficient used for associating the three-dimensional image data with the three-dimensional space, on a basis of the movement of the transmitter.

2. The ultrasound diagnosis apparatus according to claim 1, wherein the processing circuitry is configured to
   detect the movement of the transmitter by detecting a change in coordinates of the second position sensor, and
   correct the misregistration between the cross-sectional plane in the three-dimensional image data and the cross-sectional plane scanned by the ultrasound probe, by transforming coordinates of the first position sensor that is attached to the ultrasound probe and is used for registration, on a basis of a moving amount of the coordinates of the second position sensor.

3. The ultrasound diagnosis apparatus according to claim 2, wherein the processing circuitry is configured to correct the misregistration between the cross-sectional plane in the three-dimensional image data and the cross-sectional plane scanned by the ultrasound probe, by correcting the association between the three-dimensional image data and the three-dimensional space, on the basis of the moving amount of the coordinates of the second position sensor.

4. The ultrasound diagnosis apparatus according to claim 2, wherein the second position sensor is disposed on one of the following: a bed on which a subject is lying; an apparatus main body, a pole supporting the transmitter; and the subject.

5. The ultrasound diagnosis apparatus according to claim 1, wherein the processing circuitry is configured to
   detect the movement of the transmitter, by detecting a change in a correspondence relationship between coordinates of the first position sensor in a three-dimensional space generated by the transmitter and coordinates of the first position sensor in a three-dimensional space generated by a fixed transmitter that is different from the transmitter and is used for a correcting purpose, the first position sensor being attached to the ultrasound probe and used for registration, and correct the misregistration between the cross-sectional plane in the three-dimensional image data and the cross-sectional plane scanned by the ultrasound probe, by correcting the association between the three-dimensional image data and the three-dimensional space, on a basis of a change amount of the correspondence relationship.

6. The ultrasound diagnosis apparatus according to claim 5, wherein the processing circuitry is configured to use the transmitter and the fixed transmitter while interchanging the transmitters on a basis of a precision level of each of the three-dimensional spaces generated by the transmitter and the fixed transmitter.

7. The ultrasound diagnosis apparatus according to claim 1, wherein the processing circuitry is further configured to
detect movement of the transmitter on a basis of position information of the transmitter included in an image, and
correct the misregistration between the cross-sectional plane in the three-dimensional image data and the cross-sectional plane scanned by the ultrasound probe, by transforming coordinates of the first position sensor that is attached to the ultrasound probe and is used for registration, on the basis of the moving amount of the transmitter.

8. The ultrasound diagnosis apparatus according to claim 1, wherein the processing circuitry is configured to correct the misregistration between the cross-sectional plane in the three-dimensional image data and the cross-sectional plane scanned by the ultrasound probe, by correcting position information detected by the first position sensor.

9. An ultrasound diagnosis apparatus comprising:
a first position sensor configured to obtain position information in a three-dimensional space by receiving a reference signal from a transmitter;
a second position sensor fixed at an arbitrary position within the three-dimensional space and configured to obtain position information in the three-dimensional space by receiving the reference signal from the transmitter; and
processing circuitry configured to
associate three-dimensional image data generated by a medical image diagnosis apparatus with the three-dimensional space, on a basis of a registration between image data generated by the medical image diagnosis apparatus and image data scanned by an ultrasound probe attached with the first position sensor,
detect movement of the transmitter by detecting a change in coordinates of the second position sensor attached to an ultrasound probe that is disposed in an arbitrary position within the three-dimensional space generated by the transmitter and is not in operation, and
correct a misregistration between a cross-sectional plane in the three-dimensional image data and a cross-sectional plane scanned by the ultrasound probe, by transforming coordinates of the first position sensor that is attached to the ultrasound probe in operation and is used for registration, on a basis of a moving amount of the coordinates of the second position sensor.

10. A correcting method to be implemented by a computer for correcting image data, the correcting method comprising:
associating three-dimensional image data generated by a medical image diagnosis apparatus with a three-dimensional space based on a reference signal transmitted by a transmitter, on a basis of a registration between image data generated by the medical image diagnosis apparatus and image data scanned by an ultrasound probe attached with a first position sensor;
detecting movement of the transmitter within the associated three-dimensional space, on a basis of position information obtained by a second position sensor fixed at an arbitrary position within the three-dimensional space and configured to obtain the position information in the three-dimensional space by receiving the reference signal; and
correcting a misregistration between a cross-sectional plane in the three-dimensional image data and a cross-sectional plane scanned by the ultrasound probe, by correcting a transformation coefficient used for associating the three-dimensional image data with the three-dimensional space, on a basis of a moving amount of the transmitter.

* * * * *